(12) United States Patent
San Vicente et al.

(10) Patent No.: US 9,974,018 B2
(45) Date of Patent: May 15, 2018

(54) SYSTEMS AND METHODS FOR PROCESSING AND TRANSMITTING SENSOR DATA

(71) Applicant: DexCom, Inc., San Diego, CA (US)

(72) Inventors: Kenneth San Vicente, San Diego, CA (US); Hari Hampapuram, San Diego, CA (US); Eli Reihman, San Diego, CA (US); Katherine Yerre Koehler, San Diego, CA (US); Jacob S. Leach, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1091 days.

(21) Appl. No.: 13/624,727

(22) Filed: Sep. 21, 2012

(65) Prior Publication Data

US 2013/0078912 A1 Mar. 28, 2013

Related U.S. Application Data

(60) Provisional application No. 61/538,447, filed on Sep. 23, 2011.

(51) Int. Cl.
*H04B 7/24* (2006.01)
*H04W 52/02* (2009.01)
(Continued)

(52) U.S. Cl.
CPC ....... *H04W 52/0219* (2013.01); *A61B 5/0004* (2013.01); *A61B 5/0015* (2013.01); *A61B 5/0026* (2013.01); *A61B 5/14532* (2013.01); *G16H 40/63* (2018.01); *H04W 12/06* (2013.01); *H04W 52/0209* (2013.01); *H04W 76/10* (2018.02); *H04W 76/14* (2018.02); *H04W 76/25* (2018.02); *G06F 19/3418* (2013.01);
(Continued)

(58) Field of Classification Search
USPC ............... 455/42.1; 340/539.12; 709/203
See application file for complete search history.

(56) References Cited

U.S. PATENT DOCUMENTS 6,564,105 B2   5/2003   Starkweather et al.
6,571,128 B2   5/2003   Lebel et al.
(Continued)

FOREIGN PATENT DOCUMENTS

CA   2690742 A1   12/2008
EP   1445893 A2    8/2004
(Continued)

OTHER PUBLICATIONS

Dynastream Innovations, Inc.: ANT Message Protocol and Usage (Jul. 2, 2007).
(Continued)

*Primary Examiner* — Yuwen Pan
*Assistant Examiner* — Fatuma Sherif
(74) *Attorney, Agent, or Firm* — Knobbe Martens Olson & Bear, LLP

(57) ABSTRACT

Systems and methods for processing, transmitting and displaying data received from an analyte sensor, such as a glucose sensor, are provided. The data can be displayed on a hand-held display device having a display such as a key fob device including a user interface, such as an LCD and one or more buttons 604 allows a user to view data, and a physical connector, such as USB port.

12 Claims, 15 Drawing Sheets

(51) Int. Cl.
  *A61B 5/00*    (2006.01)
  *A61B 5/145*   (2006.01)
  *H04W 12/06*   (2009.01)
  *H04L 29/08*   (2006.01)
  *H04W 84/18*   (2009.01)
  *G06F 19/00*   (2018.01)

(52) U.S. Cl.
  CPC ............ *H04L 67/12* (2013.01); *H04L 67/325* (2013.01); *H04W 84/18* (2013.01); *Y02A 90/26* (2018.01); *Y02D 70/00* (2018.01); *Y02D 70/1222* (2018.01); *Y02D 70/142* (2018.01); *Y02D 70/144* (2018.01); *Y02D 70/22* (2018.01); *Y02D 70/26* (2018.01)

(56) References Cited

U.S. PATENT DOCUMENTS

| | | |
|---|---|---|
| 6,585,644 B2 | 7/2003 | Lebel et al. |
| 6,659,948 B2 | 12/2003 | Lebel et al. |
| 6,758,810 B2 | 7/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,958,705 B2 | 10/2005 | Lebel et al. |
| 7,098,803 B2 | 8/2006 | Mann et al. |
| 7,369,634 B2 | 5/2008 | Spital et al. |
| 7,406,105 B2 | 7/2008 | DlMain et al. |
| 7,587,287 B2 | 9/2009 | Connolly et al. |
| 7,595,723 B2 | 9/2009 | Heitzmann et al. |
| 7,722,536 B2 | 5/2010 | Goodnow |
| 7,742,745 B2 | 6/2010 | Twitchell, Jr. |
| 7,768,408 B2 | 8/2010 | Reggiardo et al. |
| 7,801,582 B2 | 9/2010 | Peyser |
| 7,811,231 B2 | 10/2010 | Jin et al. |
| 7,826,382 B2 | 11/2010 | Sicurello et al. |
| 7,884,729 B2 | 2/2011 | Reggiardo et al. |
| 7,948,370 B2 | 5/2011 | Reggiardo et al. |
| 7,949,404 B2 | 5/2011 | Hill |
| 8,029,443 B2 | 10/2011 | Goodnow |
| 8,036,152 B2 | 10/2011 | Brown et al. |
| 8,066,639 B2 | 11/2011 | Nelson et al. |
| 8,073,008 B2 | 12/2011 | Metha et al. |
| 8,085,151 B2 | 12/2011 | Jennewine |
| 8,086,292 B2 | 12/2011 | Peyser |
| 8,089,363 B2 | 1/2012 | Reggiardo et al. |
| 8,123,686 B2 | 2/2012 | Fennell et al. |
| 8,187,183 B2 | 5/2012 | Lin et al. |
| 8,208,973 B2 | 6/2012 | Metha et al. |
| 8,229,535 B2 | 7/2012 | Mensinger et al. |
| 8,233,456 B1 | 7/2012 | Kopikare et al. |
| 8,258,923 B2 | 9/2012 | Schulmann et al. |
| 8,372,351 B2 | 2/2013 | Ow-Wing |
| 8,437,966 B2 | 5/2013 | Connolley et al. |
| 8,483,967 B2 | 7/2013 | Harper |
| 8,629,769 B2 | 1/2014 | Bruce |
| 8,844,007 B2 | 9/2014 | Vicente et al. |
| 8,935,352 B1 | 1/2015 | Perrella |
| 9,098,114 B2 | 8/2015 | Potter et al. |
| 9,445,445 B2 | 9/2016 | Miller et al. |
| 2002/0046300 A1 | 4/2002 | Hanko et al. |
| 2004/0068230 A1 | 4/2004 | Estes et al. |
| 2004/0263354 A1 | 12/2004 | Mann et al. |
| 2005/0038680 A1 | 2/2005 | McMahon |
| 2005/0096009 A1 | 5/2005 | Ackley |
| 2005/0182306 A1 | 8/2005 | Sloan |
| 2006/0001538 A1 | 1/2006 | Kraft |
| 2006/0166629 A1 | 7/2006 | Reggiardo |
| 2007/0100222 A1 | 5/2007 | Mastrototaro et al. |
| 2007/0207750 A1 | 9/2007 | Brown |
| 2007/0231846 A1 | 10/2007 | Cosentino et al. |
| 2007/0253021 A1 | 11/2007 | Mehta et al. |
| 2007/0258395 A1 | 11/2007 | Jollata et al. |
| 2008/0031208 A1 | 2/2008 | Abishek et al. |
| 2008/0060955 A1 | 3/2008 | Goodnow |
| 2008/0092638 A1 | 4/2008 | Brenneman et al. |
| 2008/0278332 A1 | 11/2008 | Fennell |
| 2008/0294020 A1 | 11/2008 | Sapounas |
| 2008/0301436 A1* | 12/2008 | Yao et al. ............. 713/155 |
| 2008/0312518 A1 | 12/2008 | Jina et al. |
| 2008/0319296 A1 | 12/2008 | Bernstein et al. |
| 2008/0320587 A1 | 12/2008 | Vauclair et al. |
| 2009/0036760 A1 | 2/2009 | Hayter |
| 2009/0076359 A1 | 3/2009 | Peyser |
| 2009/0094680 A1 | 4/2009 | Gupta et al. |
| 2009/0105571 A1* | 4/2009 | Fennell et al. ......... 600/365 |
| 2009/0117844 A1 | 5/2009 | Furuya |
| 2009/0203982 A1 | 8/2009 | Nelson et al. |
| 2009/0216102 A1 | 8/2009 | Say et al. |
| 2009/0221261 A1 | 9/2009 | Soliman et al. |
| 2009/0237216 A1* | 9/2009 | Twitchell, Jr. ......... 340/10.1 |
| 2009/0240120 A1 | 9/2009 | Mensinger et al. |
| 2009/0240193 A1* | 9/2009 | Mensinger et al. ........ 604/66 |
| 2009/0284372 A1 | 11/2009 | Nelson et al. |
| 2009/0296742 A1 | 12/2009 | Sicurello et al. |
| 2009/0300616 A1 | 12/2009 | Siourello et al. |
| 2010/0076280 A1 | 3/2010 | Bernstein et al. |
| 2010/0076288 A1 | 3/2010 | Connray et al. |
| 2010/0076289 A1 | 3/2010 | Bernstein et al. |
| 2010/0076290 A1 | 3/2010 | Bernstein et al. |
| 2010/0076291 A1 | 3/2010 | Bernsiein et al. |
| 2010/0076292 A1 | 3/2010 | Bernstein et al. |
| 2010/0076293 A1 | 3/2010 | Bernstein et al. |
| 2010/0082266 A1 | 4/2010 | Connolly et al. |
| 2010/0082364 A1 | 4/2010 | Taub et al. |
| 2010/0110931 A1 | 5/2010 | Shim et al. |
| 2010/0217660 A1 | 8/2010 | Biswas et al. |
| 2010/0265073 A1 | 10/2010 | Harper |
| 2010/0275108 A1 | 10/2010 | Sloan et al. |
| 2010/0277342 A1 | 11/2010 | Sicurello et al. |
| 2010/0309001 A1 | 12/2010 | Connolly et al. |
| 2011/0003610 A1 | 1/2011 | Key et al. |
| 2011/0009272 A1 | 1/2011 | Mensinger et al. |
| 2011/0009727 A1 | 1/2011 | Mensinger et al. |
| 2011/0009813 A1 | 1/2011 | Rankers et al. |
| 2011/0015502 A1 | 1/2011 | Peyser |
| 2011/0015508 A1 | 1/2011 | Peyser |
| 2011/0015509 A1 | 1/2011 | Peyser |
| 2011/0044333 A1 | 2/2011 | Sicurello et al. |
| 2011/0046469 A1 | 2/2011 | Nelson et al. |
| 2011/0058485 A1 | 3/2011 | Sloan |
| 2011/0081888 A1 | 4/2011 | Waniss |
| 2011/0184265 A1 | 7/2011 | Hayter |
| 2011/0213225 A1 | 9/2011 | Bernstein et al. |
| 2011/0289497 A1 | 11/2011 | Kiaie et al. |
| 2012/0010353 A1 | 1/2012 | Watanabe et al. |
| 2012/0053428 A1 | 3/2012 | Bernstein |
| 2012/0078071 A1 | 3/2012 | Bohm et al. |
| 2012/0092168 A1 | 4/2012 | Jennewine |
| 2012/0101352 A1 | 4/2012 | Peyser |
| 2012/0101353 A1 | 4/2012 | Reggiardo et al. |
| 2012/0158907 A1 | 6/2012 | Fennell et al. |
| 2012/0232368 A1 | 9/2012 | Jin et al. |
| 2012/0245447 A1 | 9/2012 | Karan et al. |
| 2012/0260323 A1 | 10/2012 | San Vicente et al. |
| 2013/0035575 A1 | 2/2013 | Mayou et al. |
| 2013/0059541 A1 | 3/2013 | Sloan et al. |
| 2013/0078912 A1 | 3/2013 | San Vicente et al. |
| 2014/0206972 A1 | 7/2014 | Hayter et al. |
| 2014/0273821 A1 | 9/2014 | Miller et al. |

FOREIGN PATENT DOCUMENTS

| | | |
|---|---|---|
| EP | 2172863 A2 | 4/2010 |
| WO | WO 2002-071305 | 9/2002 |
| WO | WO 2006/079114 | 7/2006 |
| WO | WO 2008/106645 | 9/2008 |
| WO | WO 2009/018058 | 2/2009 |
| WO | WO 2009-051832 | 4/2009 |
| WO | WO 2009-105709 | 8/2009 |
| WO | WO 2009/105709 | 8/2009 |
| WO | WO 2009/146390 | 12/2009 |
| WO | WO 2009/146390 | 12/2009 |
| WO | WO 2009/146391 | 12/2009 |

(56) References Cited

FOREIGN PATENT DOCUMENTS

| | | |
|---|---|---|
| WO | WO 2009-146391 | 12/2009 |
| WO | WO 2010-039746 | 4/2010 |
| WO | WO 2010/039746 | 4/2010 |
| WO | WO 2012/010353 | 4/2010 |
| WO | WO 2012-010353 | 4/2012 |
| WO | WO 2012/108935 | 8/2012 |
| WO | WO 2012-108935 | 8/2012 |
| WO | WO 2013-044153 | 3/2013 |

OTHER PUBLICATIONS

Texas Instruments ncorporated: 1- and 8-Channel ANT RF Network Processors (2011).

\* cited by examiner

| Alphanumeric | 5 Bit Value | Alphanumeric | 5 Bit Value | Alphanumeric | 5 Bit Value |
|---|---|---|---|---|---|
| 0 | 0x00 | A | 0x0A | M | 0x15 |
| 1 | 0x01 | B | 0x0B | N | 0x16 |
| 2 | 0x02 | C | 0x0C | P | 0x17 |
| 3 | 0x03 | D | 0x0D | Q | 0x18 |
| 4 | 0x04 | E | 0x0E | R | 0x19 |
| 5 | 0x05 | F | 0x0F | S | 0x1A |
| 6 | 0x06 | G | 0x10 | T | 0x1B |
| 7 | 0x07 | H | 0x11 | U | 0x1C |
| 8 | 0x08 | J | 0x12 | W | 0x1D |
| 9 | 0x09 | K | 0x13 | X | 0x1E |
|   |   | L | 0x14 | Y | 0x1F |

Note: Alphanumeric Values I,O,V and Z are Excluded

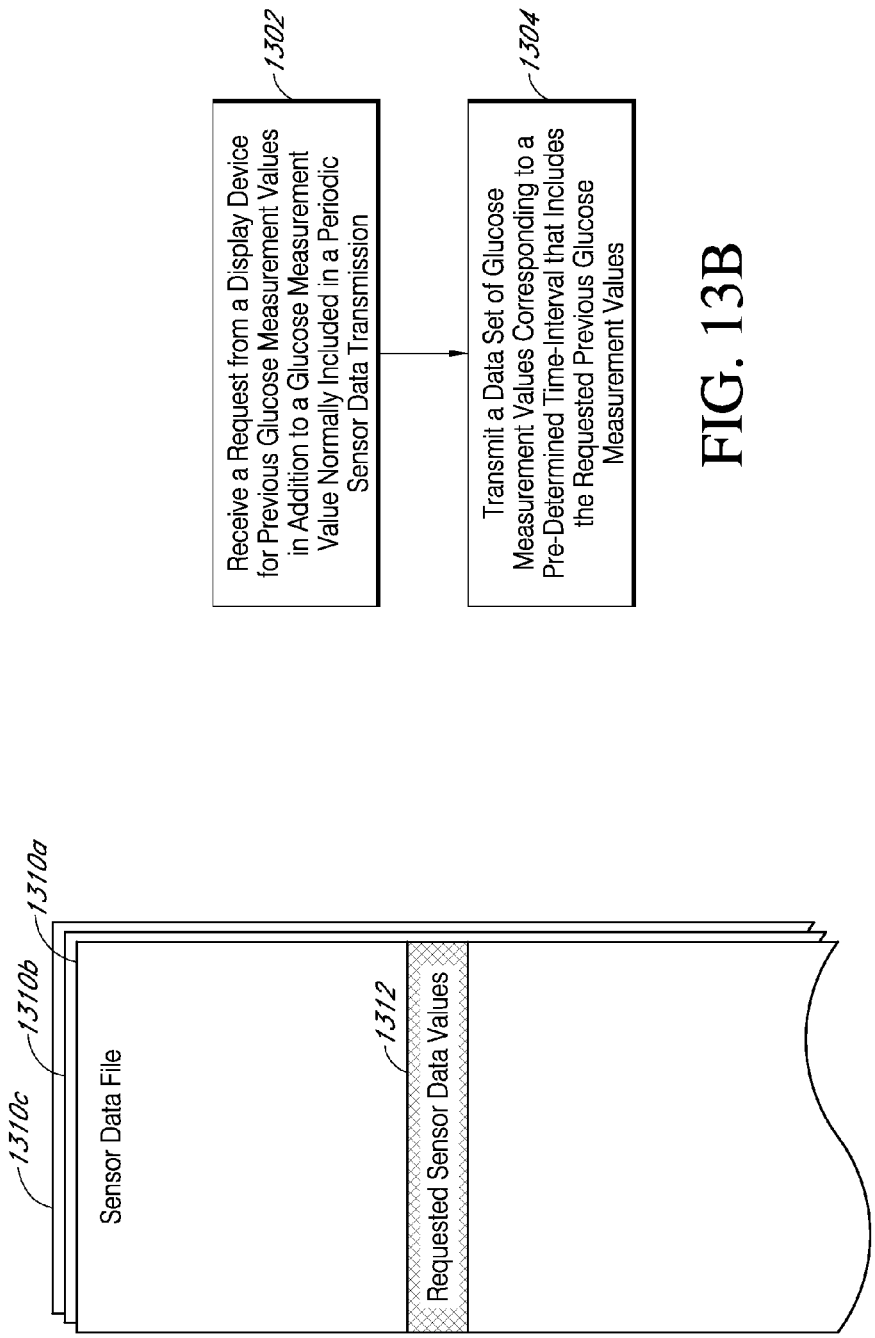

SYSTEMS AND METHODS FOR PROCESSING AND TRANSMITTING SENSOR DATA

CROSS-REFERENCE TO RELATED APPLICATION

This application claims the benefit under 35 U.S.C. § 119 (e) of U.S. provisional application Ser. No. 61/538,447, filed Sep. 23, 2011, the disclosure of which is hereby expressly incorporated by reference in its entirety and is hereby expressly made a portion of this application.

FIELD

The present invention relates generally to systems and methods for processing, transmitting and displaying data received from an analyte sensor, such as a glucose sensor.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect is provided a method for transmitting data between a first communication device associated with an analyte sensor and a second communication device configured to provide user access to analyte values and/or information derived from analyte values, comprising: activating a transceiver of a first communication device associated with an analyte sensor at a first time; establishing a two-way communication channel with the second communication device using an authentication scheme; sending analyte sensor data to the second communication device using the two-way communication channel; deactivating the transceiver of the first communication device at a second time; and periodically repeating the activating, establishing, sending and deactivating, wherein a difference between the first time and the second time is less than or equal to one minute, and wherein the periodic repeating is performed at least once every 30 minutes.

In an embodiment of the first aspect, activating comprises supplying power to the transceiver, and wherein deactivating comprises powering down the transceiver.

In an embodiment of the first aspect, activating comprises waking the transceiver from a low power sleep mode, and wherein deactivating the transceiver comprises placing the transceiver into a lower power sleep mode.

In an embodiment of the first aspect, the method further comprises closing the two-way communication channel before deactivating the transceiver.

In an embodiment of the first aspect, the difference between the first time and second time corresponds to a transmission time window, and wherein the analyte sensor data corresponds to a new glucose measurement obtained prior to a beginning of the time window, and wherein beginnings of successive time windows are separated by an update time interval.

In an embodiment of the first aspect, the method further comprises periodically measuring an analyte sensor value before each of the periodic repeating the activating, establishing, sending, and deactivating.

In an embodiment of the first aspect, the analyte sensor value comprises a glucose concentration.

In another aspect related to the first aspect, a system is provided for monitoring an analyte level of a host, the system configured to perform the method of the first aspect and/or any one or more of its embodiments, wherein the system comprises a sensor electronics module incorporating a transceiver, the sensor electronics module configured to electronically couple to an analyte sensor and generate an analyte data stream using the analyte sensor.

In a second aspect is provided a method for authorizing analyte sensor data exchange between a first communication device associated with an analyte sensor and a second communication device configured to provide user access to analyte values and/or information derived from analyte values, comprising: sending a challenge value from a first communication device associated with an analyte sensor to a second communication device; generating a first hash value in the second communication device using, at least in part, one or more of the challenge value, an identifier of the first communication device, or a key value; sending the first hash value from the second communication device to the first communication device; generating, using the first communication device, a second hash value and a third hash value; comparing, using the first communication device, the second hash value and the third hash values to the first hash value; and sending analyte sensor data only if at least one of the second hash value or the third hash values matches the first hash value.

In an embodiment of the second aspect, the method further comprises determining a type of the second communication device based on a match between the first hash value and the second hash value or a match between the first hash value and the third hash value.

In an embodiment of the second aspect, the key value is a first value if the second communication device is of a first type, and wherein the key value is a second value if the second communication device is of a second type.

In an embodiment of the second aspect, the type of second device corresponds to one of a primary device or a secondary device, wherein the primary device is configured to communicate analyte calibration data to the first communication device, and wherein the first communication device is configured to reject analyte calibration data received from a secondary communication device.

In an embodiment of the second aspect, the first hash value is generated using a display identifier.

In an embodiment of the second aspect, sending analyte sensor data comprises sending analyte sensor data based at least in part on the type of the second communication device.

In another aspect related to the second aspect, a system is provided for monitoring an analyte level of a host, the system configured to perform the method of the second aspect and/or any one or more of its embodiments, wherein a first communication device comprises a sensor electronics module, and wherein the sensor electronics module is configured to electronically couple to an analyte sensor and to generate an analyte data stream using the analyte sensor.

In a third aspect is provided a method for transmitting data between a first communication device associated with an analyte sensor and one or more second communication devices configured to provide user access to analyte values and/or information derived from analyte values, comprising: receiving a request from a second communication device of the one or more second communication devices to establish a channel for receiving analyte sensor data from the first communication device during a transmission window; and establishing a communication channel between the first communication device and the second communication device if a number of communication devices that previously received analyte sensor data from the first communication device during the transmission window is below a threshold.

In an embodiment of the third aspect, the second communication device comprises a secondary communication device.

In an embodiment of the third aspect, the method further comprises: determining whether the second communication device is a primary communication device; and establishing, if the second communication device is a primary communication device, a communication channel with the second communication device even if a number of communication devices that previously received analyte sensor data during the transmission window is equal to or greater than the threshold.

In another aspect related to the third aspect, a system is provided for monitoring an analyte level of a host, the system configured to perform the method of the third aspect and/or any one or more of its embodiments, wherein a first communication device comprises a sensor electronics module, the sensor electronics module configured to electronically couple to an analyte sensor and to generate an analyte data stream using the analyte sensor.

In a fourth aspect is provided a method for transmitting data between a first communication device associated with an analyte sensor and one or more second communication devices configured to provide user access to analyte values and/or information derived from analyte values, comprising: establishing a communication channel only with a primary device of a one or more second communication devices during a first time period within a communication window; and establishing a communication channel with one or more secondary devices of the one or more second communication devices only during a second time period different from the first time period.

In another aspect related to the fourth aspect, a system is provided for monitoring an analyte level of a host, the system configured to perform the method of the fourth aspect and/or any one or more of its embodiments, comprising a sensor electronics module configured to establish a communication channel with a primary device and establishing the communication channel with one or more secondary devices.

In a fifth aspect is provided a method for synchronizing a time for transmitting data between a first communication device associated with an analyte sensor and a primary communication device and a secondary communication device configured to provide user access to analyte values and/or information derived from analyte values, the method comprising: receiving a beacon from a first communication device at a primary communication device during a transmission time window defined by the first communication device; establishing a first communication channel between the primary communication device and a secondary communication device; transmitting beacon information from the primary communication device to the secondary communication device, wherein the beacon information comprises timing information for establishing a communication channel with the first communication device; and establishing a communication channel between the first communication device and the secondary communication device based on the beacon information.

In an embodiment of the fifth aspect, establishing a first communication channel between the primary communication device and the secondary communication device comprises executing an authentication protocol between the primary communication device and the secondary communication device.

In an embodiment of the fifth aspect, the first communication device is configured to periodically send the beacon in a series of periodic transmission time windows separated by an update time interval.

In an embodiment of the fifth aspect, the timing information comprises information about a time corresponding to the start of the transmission time window.

In another aspect related to the fifth aspect, a system is provided for monitoring an analyte level of a host, the system configured to perform the method of the fifth aspect and/or any one or more of its embodiments, wherein a first communication device comprises a sensor electronics module, the sensor electronics module configured to electronically couple to an analyte sensor and generate an analyte data stream using the analyte sensor.

In a sixth aspect is provided a method for processing data from an analyte sensor and transmitting data between a first communication device associated with an analyte sensor and a second communication device configured to provide user access to analyte values and/or information derived from analyte values, comprising: activating an analyte sensor data processing circuit and deactivating a transceiver of a first communication device associated with an analyte sensor during a first time interval; obtaining and processing analyte sensor data during the first time interval; deactivating the analyte sensor data processing circuit and activating the transceiver of the first communication device during a different second time interval; and transmitting analyte sensor data to the second communication device during the second time interval.

In an embodiment of the sixth aspect, activating and deactivating the analyte sensor data processing circuit comprises powering-up and powering-down the analyte sensor data processing circuit.

In an embodiment of the sixth aspect, activating and deactivating the analyte sensor data processing circuit comprises activating and deactivating a low power mode of the analyte sensor data processing circuit.

In an embodiment of the sixth aspect, activating and deactivating the transceiver comprises powering-up and powering-down the transceiver.

In an embodiment of the sixth aspect, activating and deactivating the transceiver comprises activating and deactivating a low power mode of the transceiver.

In another aspect related to the sixth aspect, a system is provided for monitoring an analyte level of a host, the system configured to perform the method of the sixth aspect and/or any one or more of its embodiments, wherein a first communication device comprises a sensor electronics module, the sensor electronics module configured to electronically couple to an analyte sensor.

In a seventh aspect is provided a method for processing data from an analyte sensor, comprising: obtaining and processing analyte sensor data using an analyte sensor data device associated with an analyte sensor during a first time interval; opening a transmission time window to accept requests for establishing a communication channel to communicate to the analyte sensor data device during a different second time interval, wherein the first time interval and the second time interval do not overlap.

In another aspect related to the seventh aspect, a system is provided for monitoring an analyte level of a host, the system configured to perform the method of the seventh aspect and/or any one or more of its embodiments, wherein the first communication device comprises a sensor electronics module, the sensor electronics module configured to electronically couple to an analyte sensor and generate an analyte data stream using the analyte sensor.

In an eighth aspect is provided a method for providing analyte sensor measurements from a first communication device associated with an analyte sensor to a second communication device configured to provide user access to analyte values and/or information derived from analyte values, the method comprising: receiving, from the first communication device, a request from a second communication device for previous analyte sensor measurements in addition to analyte sensor measurements of a scheduled analyte sensor measurement transmission; and transmitting to the second communication device from the first communication device a data set of analyte sensor measurements corresponding to a pre-determined time interval that includes the requested previous analyte sensor measurements.

In an embodiment of the eighth aspect, the previous analyte sensor measurements comprise a sub-set of the data set of analyte sensor measurements.

In an embodiment of the eighth aspect, the pre-determined time interval corresponds to a twenty-four hour period of analyte sensor measurements.

In another aspect related to the eighth aspect, a system is provided for monitoring an analyte level of a host, the system configured to perform the method of the eighth aspect and/or any one or more of its embodiments, wherein a first communication device comprises a sensor electronics module, the sensor electronics module configured to electronically couple to an analyte sensor and generate an analyte data stream using the analyte sensor.

In a ninth aspect is provided a method for transmitting data between a first communication device associated with an analyte sensor and a primary communication device and a secondary communication device configured to provide user access to analyte values and/or information derived from analyte values, comprising: establishing a communication channel between a secondary communication device and a first communication device during a transmission time window of a sensor session; determining whether a primary communication device has previously been in communication with the first communication device during the sensor session; and rejecting requests for data or commands sent by the secondary communication device to the first communication device if the primary communication device has not been in communication with the first device during the sensor session.

In an embodiment of the ninth aspect, the communication between the primary communication device and the first communication device comprises control information for initiating a sensor session.

In another aspect related to the ninth aspect, a system is provided for monitoring an analyte level of a host, the system configured to perform the method of the ninth aspect and/or any one or more of its embodiments, wherein the first communication device comprises a sensor electronics module, the sensor electronics module configured to electronically couple to an analyte sensor and to generate an analyte data stream using the analyte sensor.

In a tenth aspect is provided a method of transmitting data between a first communication device associated with an analyte sensor and a primary communication device and a secondary communication device, each of the primary communication device and the secondary communication device configured to provide user access to analyte values and/or information derived from analyte values, comprising: determining whether a first communication channel has been established between a first communication device and a primary communication device during a time window; and establishing a second communication channel between the first communication device and a secondary communication device during the time window only if the first communication channel was established during the time window.

In another aspect related to the tenth aspect, a system is provided for monitoring an analyte level of a host, the system configured to perform the method of the tenth aspect and/or any one or more of its embodiments, wherein the first communication device comprises a sensor electronics module, the sensor electronics module configured to electronically couple to an analyte sensor and generate an analyte data stream using the analyte sensor.

In an eleventh aspect is provided a method for transmitting data between a first communication device associated with an analyte sensor and a second communication device configured to provide user access to analyte values and/or information derived from analyte values, comprising: switching a first communication device between a plurality of transmission window states, the plurality of window transmission modes including: a first transmission window state in which the first communication device does not open a transmission window, a second transmission window state in which the first communication device periodically opens a transmission window at a first frequency, and a third transmission window state in which the first communication device periodically opens a transmission window at a second frequency that is less than the first frequency; and transmitting one or more beacons during each transmission window state.

In an embodiment of the eleventh aspect, the first communication device switches from the first transmission window state to the second transmission window state upon actuation of a hall-effect switch or a reed switch.

In an embodiment of the eleventh aspect, wherein the first communication device automatically switches from the second transmission window state to the third transmission window state responsive to a determination of a successful pairing of the first communication device with the second communication device.

In an embodiment of the eleventh aspect, the first communication device automatically switches from the second transmission window state to the third transmission window state responsive to a determination of no successful pairing after a predetermined amount of time since switching from the first transmission window state to the second transmission window state.

In an embodiment of the eleventh aspect, the first frequency is about 30 seconds and the second frequency is about 5 minutes.

In another aspect related to the eleventh aspect, a system is provided for monitoring an analyte level of a host, the system configured to perform the method of the eleventh aspect and/or any one or more of its embodiments, wherein a first communication device comprises a sensor electronics module, wherein the sensor electronics module is configured to electronically couple to an analyte sensor and generate an analyte data stream using the analyte sensor.

In a twelfth aspect is provided a method for transmitting data between a first communication device associated with an analyte sensor and second communication device configured to provide user access to analyte values and/or information derived from analyte values, the method comprising: storing technical support data in a log file in memory in a first communication device; determining that a second communication device should receive at least some of the stored technical support data; transmitting, using the first communication device, a message indicative of the determination; receiving a request from the second communication device for at least some of the stored technical support data responsive to the transmitted message; and transmitting the at least some of the stored technical support data.

In an embodiment of the twelfth aspect, the message is included in a beacon transmitted by the first communication device.

In an embodiment of the twelfth aspect, the message consists of a bit.

In another aspect related to the twelfth aspect, a system is provided for monitoring an analyte level of a host, the system configured to perform the method of the twelfth aspect and/or any one or more of its embodiments, wherein a first communication device comprises a sensor electronics module, wherein the sensor electronics module is configured to electronically couple to an analyte sensor and generate an analyte data stream using the analyte sensor.

BRIEF DESCRIPTION OF THE DRAWINGS

FIG. 13A shows an example of data structures that may be stored on an analyte sensor system that include glucose measurement values.

FIG. 13B is a flowchart of an exemplary method of transmitting sensor data from an analyte sensor system to a display device.

DETAILED DESCRIPTION

Figure 1:
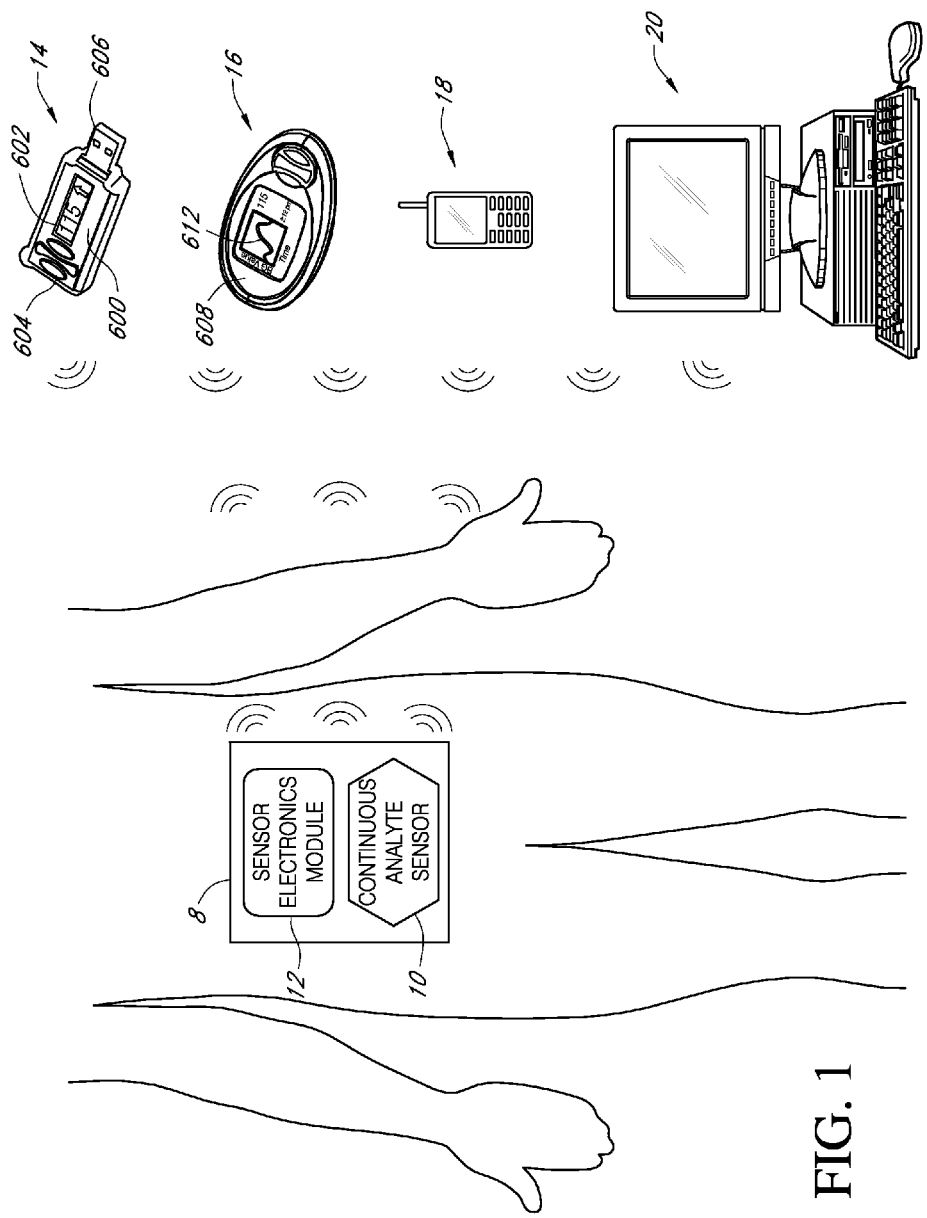
FIG. 1 is a diagram illustrating one embodiment of a continuous analyte sensor system including a sensor electronics module.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In one embodiment, the sensor electronics module includes electronics configured to process a data stream associated with an analyte concentration measured by the continuous analyte sensor in order to generate sensor information that includes raw sensor data, transformed sensor data, and/or any other sensor data, for example. The sensor electronics module may further be configured to generate sensor information that is customized for respective display devices, such that different display devices may receive different sensor information.

Alerts

In one embodiment, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In one embodiment, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. Co-pending U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data packaging indicating an alarm should be initiated by one or a plurality of display devices (e.g., sequentially and/or simultaneously). In some embodiments, the sensor electronics module determines which of the one or more alarms to trigger based on one or more alerts that are triggered. For example, when an alert triggers that indicates severe hypoglycemia, the sensor electronics module can perform multiple actions, such as activating an alarm on the sensor electronics module, transmitting a data package to a small (key fob) indicating activation of an alarm on the display, and transmitting a data package as a text message to a care provider. As an example, a text message can appear on a small (key fob) display, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device, 2) a key fob device, 3) a cell phone (via auditory and/or visual methods, such as, text message to the host and/or care provider, voice message to the host and/or care provider, and/or 911).

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In one embodiment, the sensor electronics module directly wirelessly transmits displayable sensor information to one or a plurality of display devices, such that the displayable sensor information transmitted from the sensor electronics module is received by the display device without intermediate processing of the displayable sensor information.

In one embodiment, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used with the preferred embodiments.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with the preferred embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Small (Key Fob) Display Device

In some embodiments, one the plurality of display devices is a small (e.g., key fob) display device 14 (FIG. 1) that is configured to display at least some of the sensor information, such as an analyte concentration value and a trend arrow. In general, a key fob device is a small hardware device with a built-in authentication mechanism sized to fit on a key chain. However, any small display device 14 can be configured with the functionality as described herein with reference to the key fob device 14, including a wrist band, a hang tag, a belt, a necklace, a pendent, a piece of jewelry, an adhesive patch, a pager, an identification (ID) card, and the like, all of which are included by the phrase "small display device" and/or "key fob device" herein.

In general, the key fob device 14 includes electronics configured to receive and display displayable sensor information (and optionally configured to query the sensor electronics module for the displayable sensor information). In one embodiment, the electronics include a RAM and a program storage memory configured at least to display the sensor data received from the sensor electronics module. In some embodiments, the key fob device 14 includes an alarm configured to warn a host of a triggered alert (e.g., audio, visual and/or vibratory). In some embodiments, the key fob device 14 includes a user interface, such as an LCD 602 and one or more buttons 604 that allows a user to view data, such as a numeric value and/or an arrow, to toggle through one or more screens, to select or define one or more user parameters, to respond to (e.g., silence, snooze, turn off) an alert, and/or the like.

In some embodiments, the key fob display device has a memory (e.g., such as in a gig stick or thumb drive) that stores sensor, drug (e.g., insulin) and other medical information, enabling a memory stick-type function that allows data transfer from the sensor electronics module to another device (e.g., a PC) and/or as a data back-up location for the sensor electronics module memory (e.g., data storage memory). In some embodiments, the key fob display device is configured to be automatically readable by a network system upon entry into a hospital or other medical complex.

In some embodiments, the key fob display device includes a physical connector, such as USB port 606, to enable connection to a port (e.g., USB) on a computer, enabling the key fob to function as a data download device (e.g., from the sensor electronics module to a PC), a telemetry connector (e.g., Bluetooth adapter/connector for a PC), and/or enables configurable settings on the key fob device (e.g., via software on the PC that allows configurable parameters such as numbers, arrows, trend, alarms, font, etc.) In some embodiments, user parameters associated with the small (key fob) display device can be programmed into (and/or modified) by a display device such as a personal computer, personal digital assistant, or the like. In one embodiment, user parameters include contact information, alert/alarms settings (e.g., thresholds, sounds, volume, and/or the like), calibration information, font size, display preferences, defaults (e.g., screens), and/or the like. Alternatively, the small (key fob) display device can be configured for direct programming of user parameters. In some embodiments, wherein the small (key fob) display device comprises a telemetry module, such as Bluetooth, and a USB connector (or the like), such that the small (key fob) display device additionally functions as telemetry adapter (e.g., Bluetooth adapter) enabling direct wireless communication between the sensor electronics module and the PC, for example, wherein the PC does not include the appropriate telemetry adapter therein.

Large (Hand-Held) Display Device

In some embodiments, one the plurality of display devices is a hand-held display device 16 (FIG. 1) configured to display sensor information including an analyte concentration and a graphical representation of the analyte concentration over time. In general, the hand-held display device comprises a display 608 sufficiently large to display a graphical representation 612 of the sensor data over a time period, such as a previous 1, 3, 5, 6, 9, 12, 18, or 24-hours of sensor data. In some embodiments, the hand-held device 16 is configured to display a trend graph or other graphical representation, a numeric value, an arrow, and/or to alarm the host. U.S. Patent Publication No. 2005/0203360, which is incorporated herein by reference in its entirety, describes and illustrates some examples of display of data on a hand-held display device. Although FIG. 6 illustrates one embodiment of a hand-held display device, the hand-held device can be any single application device or multi-application device, such as mobile phone, a palm-top computer, a PDA, portable media player (e.g., iPod, MP3 player), a blood glucose meter, an insulin pump, and/or the like.

In some embodiments, a mobile phone (or PDA) is configured to display (as described above) and/or relay sensor information, such as via a voice or text message to the host and/or the host's care provider. In some embodiments, the mobile phone further comprises an alarm configured to warn a host of a triggered alert, such as in response to receiving a data package indicating triggering of the alert. Depending on the embodiment, the data package may include displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, one of the display devices is a drug delivery device, such as an insulin pump and/or insulin pen, configured to display sensor information. In some embodiments, the sensor electronics module is configured to wirelessly communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Patent Publication No. 2005/0192557, which is incorporated herein by reference in its entirety. In some alternative embodiments, the sensor electronic module is configured to wirelessly communicate with a drug delivery device that does not include a display, for example, in order to enable a closed loop and/or semi-closed loop system as described above.

In some embodiments, one of the display devices is a drug delivery device is a reference analyte monitor, such as a blood glucose meter, configured to measure a reference analyte value associated with an analyte concentration in a biological sample from the host.

Personal Computer Display Device

In some embodiments, one of the display devices is personal computer (PC) 20 (FIG. 1) configured to display sensor information. Preferably, the PC 24 has software installed, wherein the software enables display and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module and the PC. In some embodiments, the PC 24 is configured to set and/or modify configurable parameters of the sensor electronics module 12 and/or small (key fob device) 14, as described in more detail elsewhere herein.

Other Display Devices

In some embodiments, one of the display devices is an on-skin display device that is splittable from, releasably attached to, and/or dockable to the sensor housing (mounting unit, sensor pod, or the like). In some embodiments, release of the on-skin display turns the sensor off; in other embodiments, the sensor housing comprises sufficient sensor electronics to maintain sensor operation even when the on-skin display is released from the sensor housing.

In some embodiments, one of the display devices is a secondary device, such as a heart rate monitor, a pedometer, a temperature sensor, a car initialization device (e.g., configured to allow or disallow the car to start and/or drive in response to at least some of the sensor information wirelessly communicated from the sensor electronics module (e.g., glucose value above a predetermined threshold)). In some alternative embodiments, one of the display devices is designed for an alternative function device (e.g., a caller id device), wherein the system is configured to communicate with and/or translate displayable sensor information to a custom protocol of the alternative device such that displayable sensor information can be displayed on the alternative function device (display of caller id device).

Exemplary Configurations

FIG. 1 is a diagram illustrating one embodiment of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14, 16, 18, and/or 20.

In one embodiment, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety.

Referring again to FIG. 1, a plurality of display devices (14, 16, 18, and/or 20) are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data.

In the embodiment of FIG. 1, the plurality of display devices includes a small (key fob) display device 14, such as a wrist watch, a belt, a necklace, a pendent, a piece of jewelry, an adhesive patch, a pager, a key fob, a plastic card (e.g., credit card), an identification (ID) card, and/or the like, wherein the small display device comprises a relatively small display (e.g., smaller than the large display device) and is configured to display certain types of displayable sensor information (e.g., a numerical value and an arrow, in some embodiments). In some embodiments, one of the plurality of display devices is a large (hand-held) display device 16, such as a hand-held receiver device, a palm-top computer and/or the like, wherein the large display device comprises a relatively larger display (e.g., larger than the small display device) and is configured to display a graphical representation of the continuous sensor data (e.g., including current and historic data). Other display devices can include other hand-held devices, such as a cell phone or PDA 18, an insulin delivery device, a blood glucose meter, and/or a desktop or laptop computer 24.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, co-pending U.S. Patent Publication No. US-2008-0108942-A1 filed on Mar. 26, 2007, and co-pending U.S. Patent Application No. US-2007-0197890-A1 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Figure 2A:
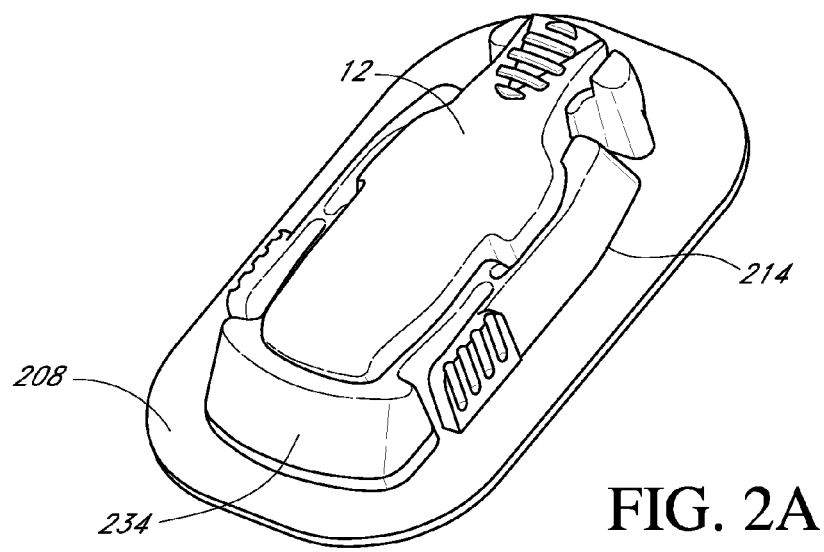
FIG. 2A is a perspective view of a sensor system including a mounting unit and sensor electronics module attached thereto according to one embodiment.
Figure 2B:
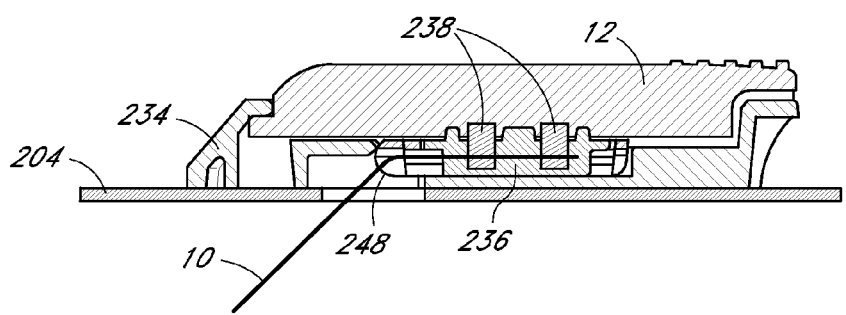
FIG. 2B is a side view of the sensor system of FIG. 2B.

FIGS. 2A and 2B are perspective and side views of a sensor system including a mounting unit 214 and sensor electronics module 12 attached thereto in one embodiment, shown in its functional position, including a mounting unit and a sensor electronics module matingly engaged therein. In some embodiments, the mounting unit 214, also referred to as a housing or sensor pod, comprises a base 234 adapted for fastening to a host's skin. The base can be formed from a variety of hard or soft materials, and can comprises a low profile for minimizing protrusion of the device from the host during use. In some embodiments, the base 234 is formed at least partially from a flexible material, which is believed to provide numerous advantages over conventional transcutaneous sensors, which, unfortunately, can suffer from motion-related artifacts associated with the host's movement when the host is using the device. The mounting unit 214 and/or sensor electronics module 12 can be located over the sensor insertion site to protect the site and/or provide a minimal footprint (utilization of surface area of the host's skin).

In some embodiments, a detachable connection between the mounting unit 214 and sensor electronics module 12 is provided, which enables improved manufacturability, namely, the relatively inexpensive mounting unit 214 can be disposed of when replacing the sensor system after its usable life, while the relatively more expensive sensor electronics module 12 can be reusable with multiple sensor systems. In some embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 238 are mounted on or in a subassembly hereinafter referred to as a contact subassembly 236 configured to fit within the base 234 of the mounting unit 214 and a hinge 248 that allows the contact subassembly 236 to pivot between a first position (for insertion) and a second position (for use) relative to the mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 238 are formed from a conductive elastomeric material, such as a carbon black elastomer, through which the sensor 10 extends.

In certain embodiments, the mounting unit 214 is provided with an adhesive pad 208, disposed on the mounting unit's back surface and includes a releasable backing layer. Thus, removing the backing layer and pressing the base portion 234 of the mounting unit onto the host's skin adheres the mounting unit 214 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety.

Use of Data Communication Protocols

Figure 3:
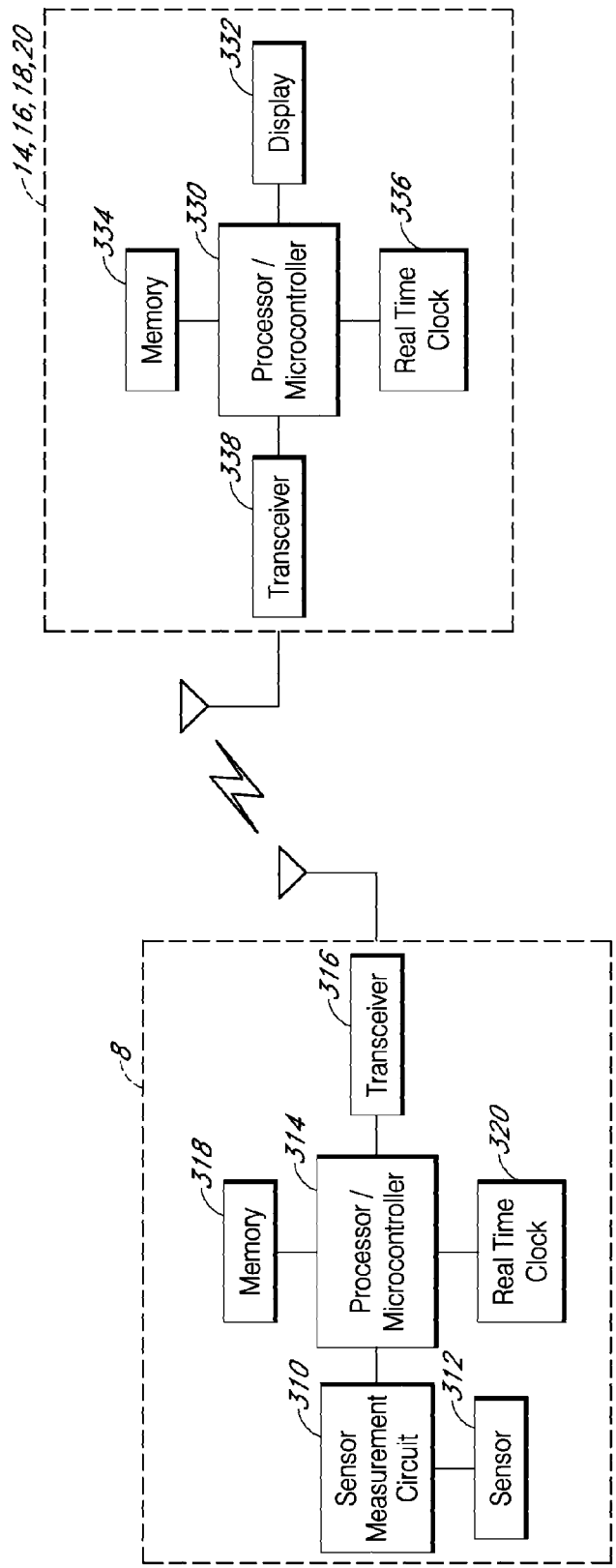
FIG. 3 is an exemplary block diagram illustrating various elements of one embodiment of a continuous analyte sensor system and display device.

FIG. 3 is an exemplary block diagram illustrating various elements of one embodiment of a continuous analyte sensor system 8 and display device 14, 16, 18, 20. The sensor system 8 may include a sensor 312 (also designated 10 in FIG. 1) coupled to a sensor measurement circuit 310 for processing and managing sensor data. The sensor measurement circuit 310 may be coupled to a processor 314 (part of item 12 in FIG. 1). In some embodiments, the processor 314 may perform part or all of the functions of the sensor measurement circuit 310 for obtaining and processing sensor measurement values from the sensor 312. The processor may be further coupled to a transceiver 316 (part of item 12 in FIG. 1) for sending sensor data and receiving requests and commands from an external device, such as the display device 14, 16, 18, 20, which is used to display or otherwise provide the sensor data to a user. The sensor system 8 may further include a memory 318 (part of item 12 in FIG. 1) and a real time clock 320 (part of item 12 in FIG. 1) for storing and tracking sensor data.

Wireless communication protocols may be used to transmit and receive data between the sensor system 8 and the display device 14, 16, 18, 20. The wireless protocol used may be designed for use in a wireless sensor network that is optimized for periodic and small data transmissions (that may be transmitted at low rates if necessary) to and from multiple devices in a close range (e.g., a personal area network (PAN)). For example, the protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The protocol may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support low power wireless communication such as peer-to-peer, start, tree, or mesh network topologies. The wireless protocol may operate in various frequency bands such as an open ISM band such as 2.4 GHz. Furthermore, to reduce power usage, the wireless protocol may adaptively configure data rates according to power consumption.

The display device 14, 16, 18, 20 may be used for alerting and providing sensor information to a user, and may include a processor 330 for processing and managing sensor data. The display device 14, 16, 18, 20 may include a display 332, a memory 334, and a real time clock 336 for displaying, storing and tracking sensor data respectively. The display device 14, 16, 18, 20 may further include a transceiver 338 for receiving sensor data and for sending requests, instructions, and data to the sensor system 8. The transceiver 338 may further employ a communication protocol.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit 316.

Components of the analyte sensor system 8 may require replacement periodically. For example, the analyte sensor system 8 may include an implantable sensor 312 that may be attached to a sensor electronics module that includes the sensor measurement circuit 310, the processor 314, memory 318, and transceiver 316, and battery (not shown). The sensor 312 may require periodic replacement (e.g., every 7-30 days). The sensor electronics module may be configured to be powered and active for much longer than the sensor 312 (e.g., for six months or more) until the battery needs replacement. Replacing these components may be difficult and require the assistance of trained personnel. Reducing the need to replace such components, particularly the battery, significantly improves the convenience of the analyte sensor system 8 to the user. In some embodiments, the sensor session as defined above may correspond to the life of the sensor 312 (e.g., 7-30 days). When a sensor electronic module is used for the first time (or reactivated once a battery has been replaced in some cases), it may be connected to a sensor 312 and a sensor session may be established. As will be further described below, there may be a process for initially establishing communication between a display device 14, 16, 18, 20 and the sensor electronics module when it is first used or re-activated (e.g., the battery is replaced). Once the display device 14, 16, 18, 20 and sensor electronics module have established communication, the display device 14, 16, 18, 20 and sensor electronics module may periodically and/or continuously be in communication over the life of several sensors 312 until, for example, the battery needs to be replaced. Each time a sensor 312 is replaced, a new sensor session may be established. The new sensor session may be initiated through a process completed using a display device 14, 16, 18, 20 and the process may be triggered by notifications of a new sensor via the communication between the sensor electronics module and the display device 14, 16, 18, 20 that may be persistent across sensor sessions.

The analyte sensor system 8 gathers analyte data from the sensor 312 that it periodically sends to the display device 14, 16, 18, 20. Data points are gathered and transmitted over the life of the sensor (e.g., 1-30 days or more). New measurements may need to be transmitted often enough to adequately monitor glucose levels. Rather than having the transmission and receiving circuitry of each of the sensor system 8 and display device 12, 16, 18, 20 continuously communicating, the analyte sensor system 8 and display device 14, 16, 18, 20 may regularly and periodically establish a communication channel between them. Thus, sensor system 8 can communicate via wireless transmission with display device 14, 16, 18, 20 (e.g., a hand-held computing device) at predetermined time intervals. The duration of the predetermined time interval can be selected to be long enough so that the sensor system 8 does not consume too much power by transmitting data more frequently than needed, yet frequent enough to provide substantially real-time sensor information (e.g., measured glucose values) to the display device 14, 16, 18, 20 for output (e.g., display) to a user. While the predetermined time interval is every five minutes in one embodiment, it is appreciated that this time interval can be varied to be any desired length of time.

Figure 4A:
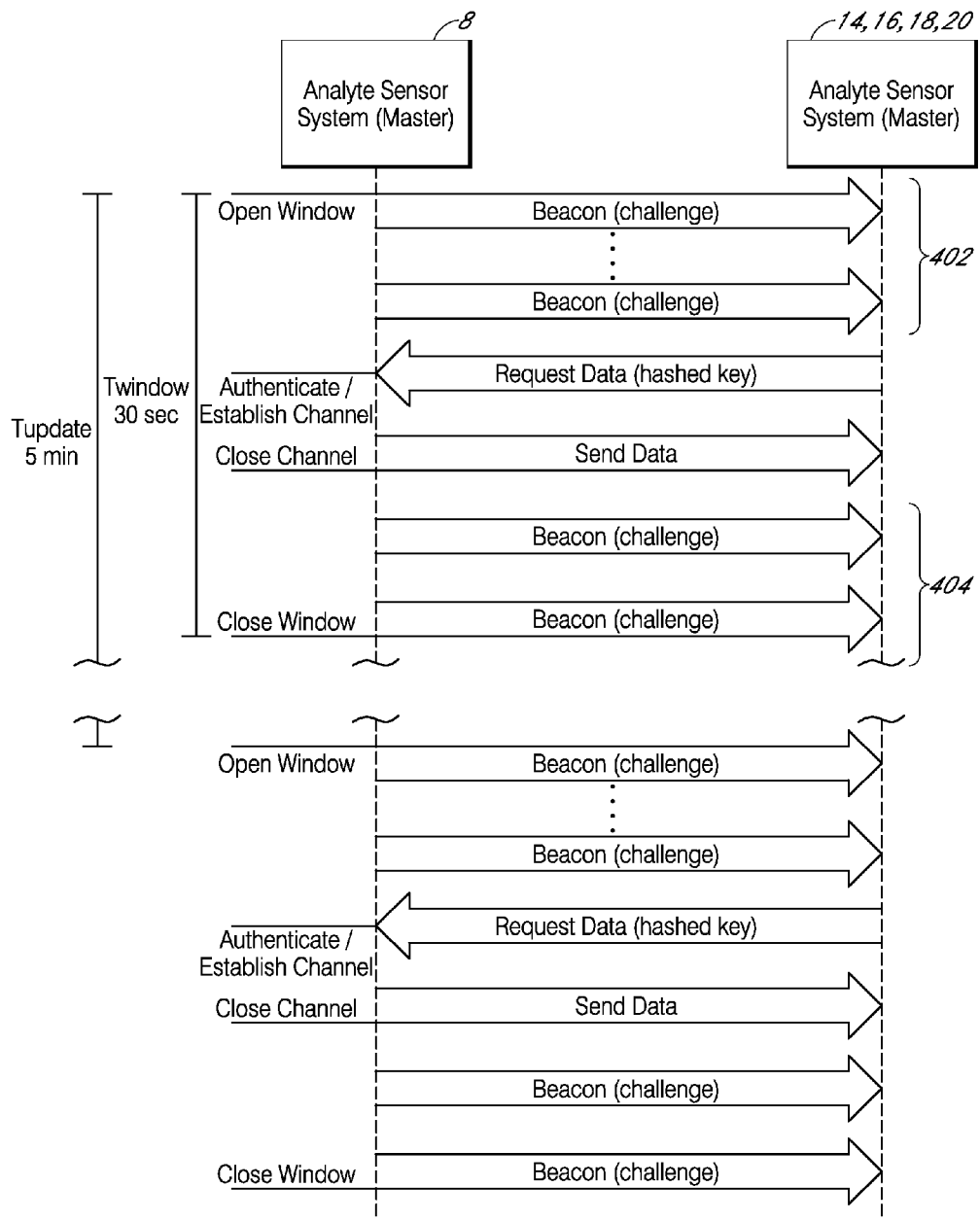
FIG. 4A is a flow diagram of an exemplary communication between an analyte sensor system and a display device for communicating glucose measurement values.

FIG. 4A is a flow diagram of an exemplary communication between an analyte sensor system 8 and a display device 14, 16, 18, 20 for communicating glucose measurement values. The data transfer may happen periodically, at times separated by an update interval $T_{update}$ that may correspond to a period of obtaining and sending a recently measured glucose value (e.g., five minutes). In between these data transfer procedures, the transceiver 316 of the analyte sensor system 8 can be powered down or in a sleep mode to conserve battery life. As such, the analyte sensor system 8 may therefore establish a communication channel with the display device 14, 16, 18, 20 once per update interval $T_{update}$. Establishing a communication channel may occur during a transmission window $T_{window}$ within an update interval $T_{update}$.

To establish a communication channel, the analyte sensor system 8 may send one or more message beacons during of a transmission window $T_{window}$ within an update interval $T_{update}$. Each message beacon may be considered an invitation for a display device 14, 16, 18, 20 to establish a communication channel with the sensor system 8. A beacon may include data including a challenge value for authenticating a display device 14, 16, 18, 20 as will be further described below. During initial system set up, the display device 14, 16, 18, 20 may listen continuously until such a message beacon is received. When the beacon is successfully received, the display device 14, 16, 18, 20 can acknowledge the reception to establish communication between the devices. As will be further described below, in response to the beacon, the display device 14, 16, 18, 20 may send a message requesting a measurement along with a computed value for authentication. Once authenticated, the analyte sensor system 8 and display device 14, 16, 18, 20 may exchange information to determine how data will be exchanged (e.g., a specific frequency, time slot assignment, etc.). When the desired data communication is complete, the channel can be closed, and the transceiver 316 of the analyte sensor system 8 (and possibly the transceiver 338 of the display device 14, 16, 18, 20 as well) can be powered down. The entire data transmission window interval $T_{window}$ for providing data to one or more display devices 14, 16, 18, 20 may be a small fraction of the update interval $T_{update}$. For example, $T_{update}$ may be five minutes and the data transmission window interval $T_{window}$ may be thirty seconds. As such, the transceiver 316 of the analyte sensor system 8 may only be powered for substantially 30 seconds of a five minute $T_{update}$ interval. This may significantly reduce power consumption. In some cases, the transceiver 316 is not completely powered down, but enters a low-power mode when not transmitting. After a $T_{update}$ interval has elapsed, the transceivers 316, 338 can be synchronized to power up again substantially simultaneously, and establish a new communication channel using the same process to exchange any new data as shown in FIG. 4A. This process may continue, with new communication channels being established at the predetermined intervals.

To allow for some loss of synchronization between the two devices in between transmissions, the analyte sensor system 8 may be configured to send a series of message beacons 402 in a window of time around the scheduled transmission time (e.g., 8 message beacons per second for 4 seconds). Any one of the message beacons can be used to initiate the establishment of a new communication channel when it is received by the display device 14, 16, 18, 20. After communicating with one device during the transmission window, the analyte sensor system 8 may send out further message bacons 404. These beacons can be received and used to establish other communication channels with other devices (e.g., other display devices) during the transmission window $T_{window}$. However, in some embodiments, if it is known that the analyte sensor system 8 is only communicating with a single display device, then the transmission window $T_{window}$ can be terminated at the same time as closing the communication channel with the display device.

Figure 4B:
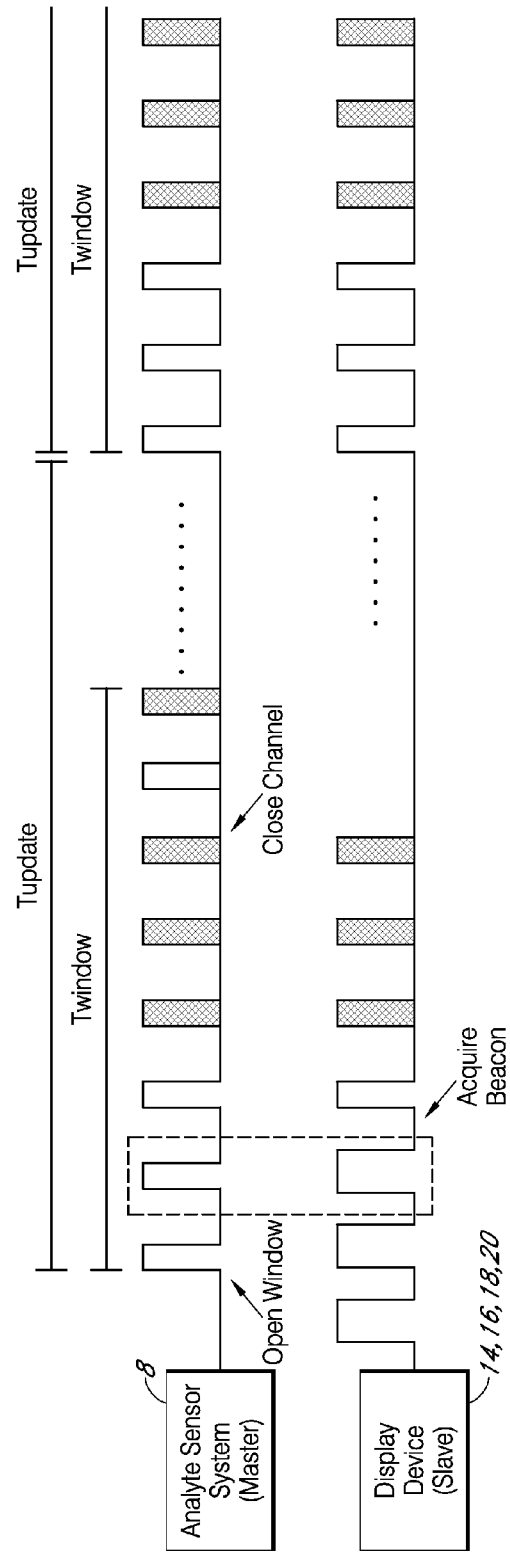
FIG. 4B is a timing diagram of en exemplary sequence for establishing a communication channel between an analyte sensor system and a display device.

FIG. 4B is a timing diagram of an exemplary sequence for establishing a communication channel between an analyte sensor system 8 and a display device 14, 16, 18, 20. The display device 14, 16, 18, 20 may initially "wake up" its transceiver 316 and wait to receive a beacon from the analyte sensor system 8. Once the analyte sensor system 8 begins sending beacons, it may take one, two, or more beacons for the display device 14, 16, 18, 20 to receive the beacon and respond with a request. Once the beacon is received and the request sent, data may thereafter be sent and/or received as shown by the shaded time slots. The channel can then be closed once analyte sensor system 8 and display device 14, 16, 18, 20 determine that all requested data has been transmitted to the respective devices or it the transmission window time expires. At the start of a new $T_{update}$ interval, the process is repeated.

Continuously re-establishing a new communication channel to allow for partially or wholly powering down the transceiver 316 during each update interval $T_{update}$ can provide significant power savings and can allow the sensor electronics module 12 to operate continuously for six months or more without requiring a battery replacement. Furthermore, rather than blindly transmitting glucose data points during the transmission window $T_{window}$, communication channels may be established so that only the desired display devices 14, 16, 18, 20 may receive the glucose information. This may prevent unauthorized use and interception of glucose measurement values. In addition, by establishing a secure two-way communication channel, requests for specific glucose measurement values or communication of calibration or configuration information may be transmitted on an as-needed/requested basis between the sensor system 8 and display device 14, 16, 18, 20.

Also, in some embodiments, the communication window need not open during every update interval $T_{update}$. Instead, the window can open every second, third or fourth update interval $T_{update}$, for example, so that communication between the sensor system 8 with the display device 14, 16, 18, 20 occurs less frequently than every update interval $T_{update}$. Doing so can further reduce power consumption. Accordingly, a window frequency variable $F_{window}$ can be used that dictates a frequency the window opens.

In some embodiments, the update interval $T_{update}$, transmission window $T_{window}$ and/or window frequency $F_{window}$ may be variable. $T_{update}$, $T_{window}$ and/or $F_{window}$ can be user configurable (e.g., by inputting a value for the variable using user interface of display device 14, 16, 18, 20) and/or automatically varied by the sensor system 8 or display device 14, 16, 18, 20 based on one or more criteria. The criteria can include: (i) a monitored battery power of the sensor system 8, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 8 or display device 14, 16, 18, 20, and (x) type of display device.

$T_{update}$, $T_{window}$ and/or $F_{window}$ and other configuration items described herein may form part of a communication protocol profile that may be stored on any device that implements the fundamental communication protocol to allow for a customized use of the protocol for receiving glucose measurement values, such as sensor system 10 and display device 14, 16, 18, 20.

Figure 5:
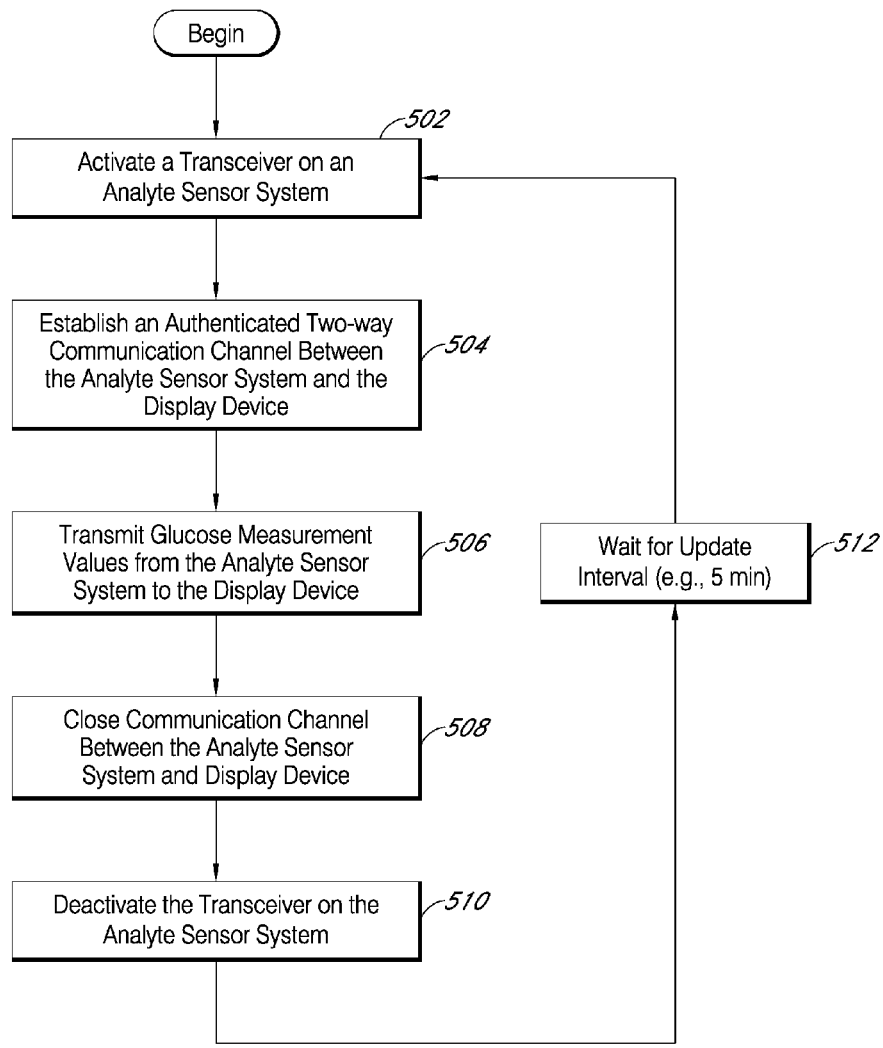
FIG. 5 is a flowchart of an exemplary method for sending glucose measurement values from an analyte sensor system to a display device.

FIG. 5 is a flowchart of an exemplary method for sending glucose measurement values from an analyte sensor system 8 to a display device 14, 16, 18, 20. At a pre-determined time in an update interval $T_{update}$, an analyte sensor system 8 may activate a transceiver 316 as shown in block 502. This may include powering the transceiver 316 or awakening the transceiver 316 from a low power mode/state such as a sleep mode. In block 504, the transceiver 316 may open and establish an authenticated two-way communication channel between the analyte sensor system 8 and a display device 14, 16, 18, 20. If the channel is established, in block 506, the analyte sensor system 8 and the display device 14, 16, 18, 20 may transmit information between them, either automatically (e.g., device determines a triggering event to transmit specific information) or in response to a request received from the other device. Such information can include one or more glucose measurement values, calibration information, alert settings, communication synchronization information, and the like. Once the transmission is complete and data requested by the display device 14, 16, 18, 20 and sensor system 10 is sent, the analyte sensor system 8 may close the communication channel. In block 510, the analyte sensor system 8 may deactivate the transceiver 316 such as powering-down the transceiver or causing it to go into a low power mode. The operations in block 504 through 508 may be repeated with additional display devices until the transmission window $T_{window}$ closes. The analyte sensor system 8 may then wait for the next transmission window $T_{window}$ to open as shown in block 512, and in the meantime gather glucose measurement values, before the process is repeated continuously over the duration of a sensor session (e.g., corresponding to the life of non-durable sensor). Between each transmission window $T_{window}$, a new analyte sensor measurement may be obtained and stored for transmission.

Sensor Electronics Unit Window Transitioning

In some embodiments, the sensor electronics module 12 can be placed in a mode wherein transmission windows occur more frequently than during normal use. This can be useful a new device is to be paired with the sensor electronics module, for example, to speed up pairing between devices.

In some implementations, when the sensor electronics module 12 is first used, a display device with which a user wants to pair the sensor electronics module does not have information about when the sensor electronics module will next open a transmission window $T_{window}$. Further, the window frequency $F_{window}$ may be low, such as a window opening only every 5 minutes. As a consequence, a display device may not be able to be paired with the sensor electronics module for nearly five minutes if the display device is constantly listening for beacons from the sensor electronics module. This can result in a long pairing process that expends valuable power due.

Accordingly, in some implementations, the sensor electronics module 12 can be switched (manually or automatically) from a first state to a second state to facilitate pairing, wherein the window frequency $F_{window}$ is greater in the second state than in the first state. After paring, the sensor electronics module 12 can then switch back to the first state or switch to a third state that has a window frequency that is different from the first state and the second state. The sensor electronics module can switch back to the first state or to the third state automatically in response to the sensor electronics module determining a successful pairing between the two devices, or switched back to the first state or to the third state manually by a user via an external switch or user input using an electronics user interface. In one implementation, the first state corresponds to a storage mode in which window frequency $F_{window}$ is 0 (i.e. transmission window is not entered to conserve power) and the third state corresponds to a normal operational state in which window frequency $F_{window}$ is greater than zero, but less than the second state. As one non-limiting example, window frequency $F_{window}$ during the second state can be 30 seconds and the window frequency $F_{window}$ during the third state can be 5 minutes.

The following is a non-limiting exemplary implementation to illustrate switching the window frequency $F_{window}$ for power savings and to facilitate pairing. As discussed above, the sensor electronics module 12 can be a separate unit that is configured to be connected to a continuous analyte sensor 10 as discussed above and illustrated in FIGS. 2A and 2B, for example. The sensor electronics module 12 can be manufactured and then stored in a container, such as a box, prior to use. To conserve power, the sensor electronics module 12 can be placed in a low power state while in the container and thereafter switched to pairing state after removal of the sensor electronics unit from the storage container.

The sensor electronics module 12 can be kept in the low power state through use of an external magnet and a reed switch or hall-effect switch within the sensor electronics module. Using an external magnet to keep a sensor electronics module in a low power mode is described in more detail in U.S. patent application Ser. No. 13/247,856 filed on Sep. 28, 2011, the content of which are hereby incorporated by reference in its entirety. A magnet can be placed next to the sensor electronics module 12 during manufacturing next to the sensor electronics module 12 in the container to keep the sensor electronics module in the low power state while in the container. When it is desired to use the sensor electronics module 12, the sensor electronics module 12 can be removed from the container and the magnet removed from the proximity of the sensor electronics module to cause the sensor electronics module to switch to the pairing state. A reed switch, hall-effect switch or the like can reside in the sensor electronics module to trigger the switching of the sensor electronics module from the low power state to the pairing state, for example.

Accordingly, the sensor electronics module 12 can be in the low power state while in storage, switched to the pairing state when removed from storage (e.g. by removing a magnet) and then switched to a normal operational state once the sensor electronics module 12 is paired with a display device. The low power state can include keeping the transceiver powered off or otherwise in a low power state wherein no beacons are transmitted. The pairing state can include a high window frequency $F_{window}$, such as every 30 seconds, wherein one or more beacons are transmitted during each window. The normal operational state can include a relatively low window frequency $F_{window}$, such as every 5 minutes, for opening a communication channel with one or more display devices to exchange information, including sensor data values.

Further, in some implementations of the above-described beacon interval transition process, the sensor electronics module will automatically change from the high window frequency $F_{window}$ used to facilitate paring (e.g., the second state) to the normal operational window frequency $F_{window}$ (e.g., the third state) after a predetermined amount of time, such as 1 hour, should a successful pairing not occur within that time. This way, valuable battery power is not wasted by having a high window frequency $F_{window}$ for an extended period of time.

Display Device Window Transitioning

In some embodiments, the display device 14, 16, 18, 20 is configured through software instructions executed by a processor of the display device to vary windows for listening for a beacon from sensor electronics module 12. Doing so can conserve battery power as opposed to constantly having the display device listen for a beacon from the sensor electronics module.

In some implementations, a state based approach for RF windowing can be used. The following is an example of states and substrates that can be used in an implementation, but it is understood that more or fewer of these states and substrates can be used depending upon the particular needs of a user. Further, it should be understood that, while this example provides times for the windowing, other times can be used depending upon the particular needs of a user and device properties. This example also contemplates implementations wherein the display device has a software application stored on the display device (which may be referred to herein as an "app") that is configured to cause the display device to request data from the sensor electronics module. The application may run as a background process on the display device and, while it is run in the background, the display device does not listen for beacons. States and substrates in this example are the following:

1. RFWindowState.Search: When this state is entered, the display device opens up the RF window for the same or slightly greater period than the window frequency of the sensor electronics unit during normal operation so at least one beacon is to be received within this period. For example, if the windowing frequency of the sensor electronics module is 5 minutes, the window in this state can be set to be open for 5 minutes and 5 seconds. This state is entered:
   a. When the display device has been in RFWindowState.Idle mode for 30 minutes; OR
   b. When the display device is in RFWindowState.Idle and the app is brought up from background.
2. RFWindowState.PairingSearch: This is very similar to RFWindowState.Search and opens up the RF window for a slightly longer period than the window frequency of the sensor electronics unit during normal operation to ensure at least one beacon cycle falls within this timeframe. The window can be open for 5 minutes and 5 seconds, for example. This state is entered:
   a. When the user enters a new transmitter id (as discussed in more detail under the heading Transceiver Pairing Authentication Scheme); OR
   b. When the display device has been in RFWindowState.PairingIdle mode for 30 minutes; OR
   c. When the display device is in RFWindowState.PairingIdle and the app is brought up from background
3. RFWindowState.Locked: This is a state when the display device has received a beacon recently, and has a good estimate of when to expect the next beacon. This includes situations where the display device has missed receiving any beacons during less than six consecutive previous beaconing windows ("beaconing cycles") from the sensor electronics module. This state has the following sub-states:
   a. RFWindowSubstateId.OpenWaitingForBeacon: This is entered when the RF window is opened while in RFWindowState.Locked state. This event is triggered by a timer in the display device for waiting for the next beacon cycle to go off while in RFWindowSubstateId.ClosedWaitingForNextBeacon sub-state.
   b. RFWindowSubstateId.PageExchange: This is entered when a beacon is received while in RFWindowState.Search, RFWindowState.PairingSearch, or RFWindowState.Locked (sub-state RFWindowSubstate.OpenWaitingForBeacon) states.
   c. RFWindowSubstateId.ClosedWaitingForNextBeacon: This state is entered when the display device has finished processing all data packet exchanges for a current transmission window.
4. RFWindowState.Idle: This state is entered when:
   a. The display device is in RFWindowState.Locked state, but has missed 6 beacon cycles OR
   b. The display device did not get any beacons in RFWindowState.Search state for 5 m 5 s.
The display device stays in RFWindowState.Idle for 30 minutes or until the user activates the app, at which point RFWindowState. Search state is entered.
5. RFWindowState.PairingIdle: This state is entered when:
   a. The display device did not get any beacons in RFWindowState.PairingSearch state for 5 m 5 s
6. RFWindowState.Inactive: This is the state when the display device does not have a transmitter id entered (i.e. it is zero).

Transceiver Pairing Authentication Scheme

In some embodiments, pairing of two devices (e.g., a master and slave device) may be required to establish a relationship between two devices that want to communicate with one another. Pairing may be accomplished during the channel establishment process described above between the two devices. Establishing a channel may involve broadcasting a unique ID by one device and a search and acquisition of this ID by another device.

A parameter that may be used in device pairing is the master device ID. In order to establish a communication channel, a master transmitter may broadcast its device ID (along with some other information) in the above described beacon and the receiver checks for the presence of the device ID of the transmitter with which it wants to communicate in the received beacons. The device ID may be a 2-byte value representing a specific master device, for example.

Although a master device ID may provide some level of security, in that a slave device can be programmed to communicate only with a master device having a particular device ID number, additional security can be useful in some embodiments. As described above, to save power by deactivating the transceiver 316 of the analyte sensor system 8, a communication channel may be re-established during each update interval $T_{update}$. As such, as part of the channel establishment process, regular and repeated re-authentication may also be provided.

To provide additional security, some embodiments of the present invention can use two pieces of information to pair a receiver with a particular transceiver device. These two pieces of information include the device ID described above and another value which is referred to herein as a sensor security code. The device ID is used as described above to filter receipt of non-matching messages at the lowest layer of the protocol stack. The sensor security code is used for a key based authentication scheme at the software application layer of the system. In some embodiments, both the device ID and the sensor security code can be derived from an identifier (e.g., a manufacturer's serial number) associated with the sensor system 8 per the description below.

As seen in the embodiment of FIG. 1, the sensor system 8 comprises two fundamental components, the continuous sensor 10 and the electronics module 12. These two components may be separable from one another, allowing, for example, replacement of the continuous sensor portion 10. In this case, the identifier may be etched into, printed on or otherwise attached to a housing of the electronics module portion 12.

The sensor system 8 may include seven alphanumeric characters printed on a housing of the sensor system 8, which can comprise the identifier used for identification purposes. This alphanumeric series of characters may be used to generate both the device ID used in the master beacons to establish a channel and to generate the sensor security code used for additional security in the glucose monitoring system. To maintain good data security, the alphanumeric characters and the sensor security code need not be transmitted over a wireless communication channel at any time.

Figures 6A, 6B:
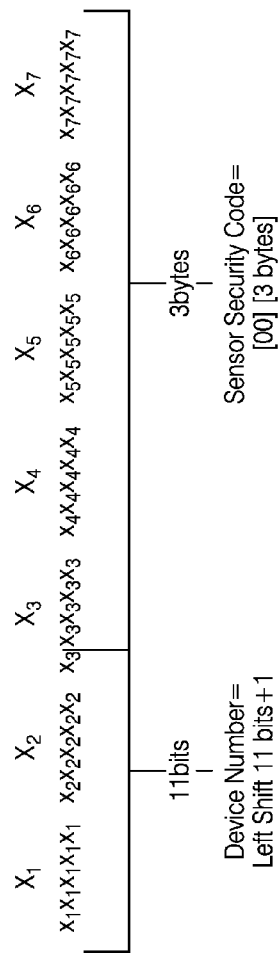
FIG. 6A provides an example of mapping an alphanumeric character to a five bit binary value.
FIG. 6B provides an example of mapping a 35 bit value to a device number and a transmitter ID.

In some embodiments, the seven alphanumeric characters are converted to seven 5 bit binary values as shown for example in FIG. 6A. These 35 bits are then concatenated together and divided into a device ID and sensor security code as shown for example in FIG. 4B. The most significant 11 bits, used for the device ID, are left-shifted by one bit and a one is inserted on the right, to produce a 12 bit value. Inserting the 1 on the right prevents the device number from being set to 0x0000. To produce a 16-bit device ID value, for example, four zeros can be used for the four most significant bits of the sequence. The remaining 24 bits of the original 35 concatenated bits can be used for the sensor security code.

As an example, a given seven character alphanumeric ID, 'A65834F', is converted to binary as follows using the binary mappings shown in FIG. 6A,

A=01010
6=00110
5=00101
S=11010
3=00011
4=00100
F=01111

These binary values are concatenated to produce a 35 bit sequence:
01010001100010111010000110010001111

This 35 bit sequence is then separated to produce:
01010001100 and 010111010000110010001111

The device ID becomes 0000 0101 0001 1001 after a one is added as the least significant bit, and four zeros are added as the most significant bits. The other 24 bits are padded on the left with eight zeros to become the four byte value 0000 0000 0101 1101 0000 1100 1000 1111.

Therefore, the device ID becomes the two byte array [0x05][0x19] used as described above in the low level standardized communication protocol. The sensor security code becomes the four byte array [0x00][0x5D][0x0C][0x8F], used as described below.

When the analyte sensor system 8 is initially set up, the identifier associated with the system is entered into the display device 14, 16, 18, 20. Now, the sensor system 8 and the display device 14, 16, 18, 20 can each compute the same device ID and sensor security code using the algorithm described above.

Figure 7:
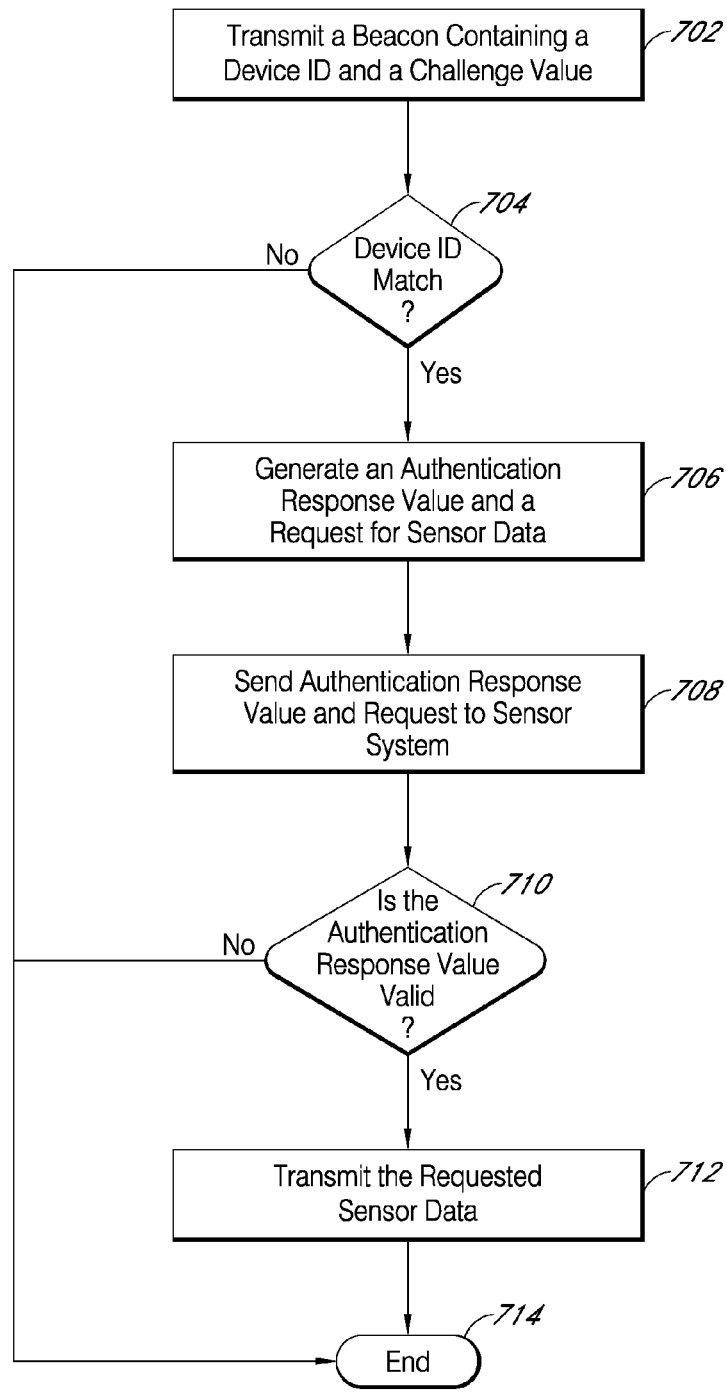
FIG. 7 is a flowchart illustrating one embodiment of an aspect of a process for pairing a transmitter with a receiver.

FIG. 7 is a flowchart illustrating one embodiment of an aspect of a process for pairing a transmitter with a receiver using a device ID and sensor security code. In block 702, the transceiver in the sensor system 8 sends one or more message beacons that include the device ID and a challenge value used in conjunction with the sensor security code as will be described below. In block 704, the display device 14, 16, 18, 20 may receive the transmission and determine whether to pair with the sensor system 8 by checking for a match between the device ID in the received beacon and the device ID it is searching for. If the device ID does not match, the pairing process can end, as shown in block 714. If the device ID does match, a communication channel is established. The part of the communication process involved in establishing a communication channel may be handled by the transceiver circuitry 316, 338 in accordance with the protocols established for the standardized communication and embedded in the transceiver circuitry. The processor 330 need not manage or even be aware of received beacons that do not contain the appropriate device ID.

If a communication channel is established, the challenge value is provided to the processor 330 to perform an additional authentication process as will now be described. The display device 14, 16, 18, 20 processes the challenge value using a predetermined algorithm and the sensor security code to produce an authentication response value as shown in block 706, as well as generating a request for sensor data. In block 708, a hashed value that includes the authentication response value as other information as described below is transmitted back to the sensor system 8 along with the request for sensor data. Sending a hashed value may avoid ever sending analyte sensor system 8 or display device 14, 16, 18, 20 identity information directly. In block 710, the sensor system 8 receives and verifies the hashed value including the authentication response value sent by the display device 14, 16, 18, 20 using the same algorithm and sensor security code. If the authentication response value is valid, the sensor system 8 transmits the requested sensor data to the display device 14, 16, 18, 20 as shown in block 712. Otherwise, as shown in block 714, the pairing process can end.

By using the method described with both the device ID and a sensor security code for communication authentication, two benefits can be obtained. First, security can be improved over using the device ID alone as authentication, because one weak link in device ID security is that the device ID is transmitted over the air in the message beacons. When the device ID is transmitted over the air, it could be intercepted by a hacker or other unauthorized user, and used to create a false receiver that could query the sensor system for user data. In addition, computational efficiency can be improved because devices without matching device IDs need not authenticate with a receiver device using the challenge/response protocol before discovering that no communication channel should be opened between the devices.

Primary and Secondary Display Devices

In some cases, the type of data exchanged between the analyte sensor system 8 and the display device 14, 16, 18, 20 may depend on the type of display device 14, 16, 18, 20. For example, some display devices 14, 16, 18, 20 may be configured to communicate calibration data to an analyte sensor system 8 and may have additional functionality for initiating new sensor sessions, setting certain alert thresholds and the like. Such a device may be referred to as a "primary" display device. In some cases, the primary display device may correspond to the device specially configured for use with the analyte sensor system 8 by a manufacturer. The primary display device may be used to configure and set up each new sensor session after sensor components have been replaced.

In some embodiments, other display devices may have less functionality and may be provided by generic electronic devices including communication circuitry that may communicate with the analyte sensor system 8 using an established base communication protocol. These display devices may be referred to as "secondary" devices, and may include general purpose smart phones, smart sports watches, general purpose tablet computers, etc. The secondary display devices may not be permitted to communicate calibration data with the analyte sensor system 8 and may be restricted in the type of data that may be requested and received. A reason for this may because the secondary display device is not approved for all of the functionality of a primary device by a regulatory agency, safety, reliability and the like.

In some embodiments, a secondary display device may display analyte values, display graph or trend arrows, provide audible alerts, or provide additional ways for providing a user with information about glucose measurement values, but not be permitted to provide calibration information to the analyte sensor system 8, for example.

In some embodiments, authentication may depend on the type of display devices and the authentication process may allow for detecting the type of display device.

For illustration purposes only, a primary device may be referred to herein as display device 16 and a secondary display device may be referred to as to one or display devices 14, 18 and 20 of FIG. 1.

Figure 8:
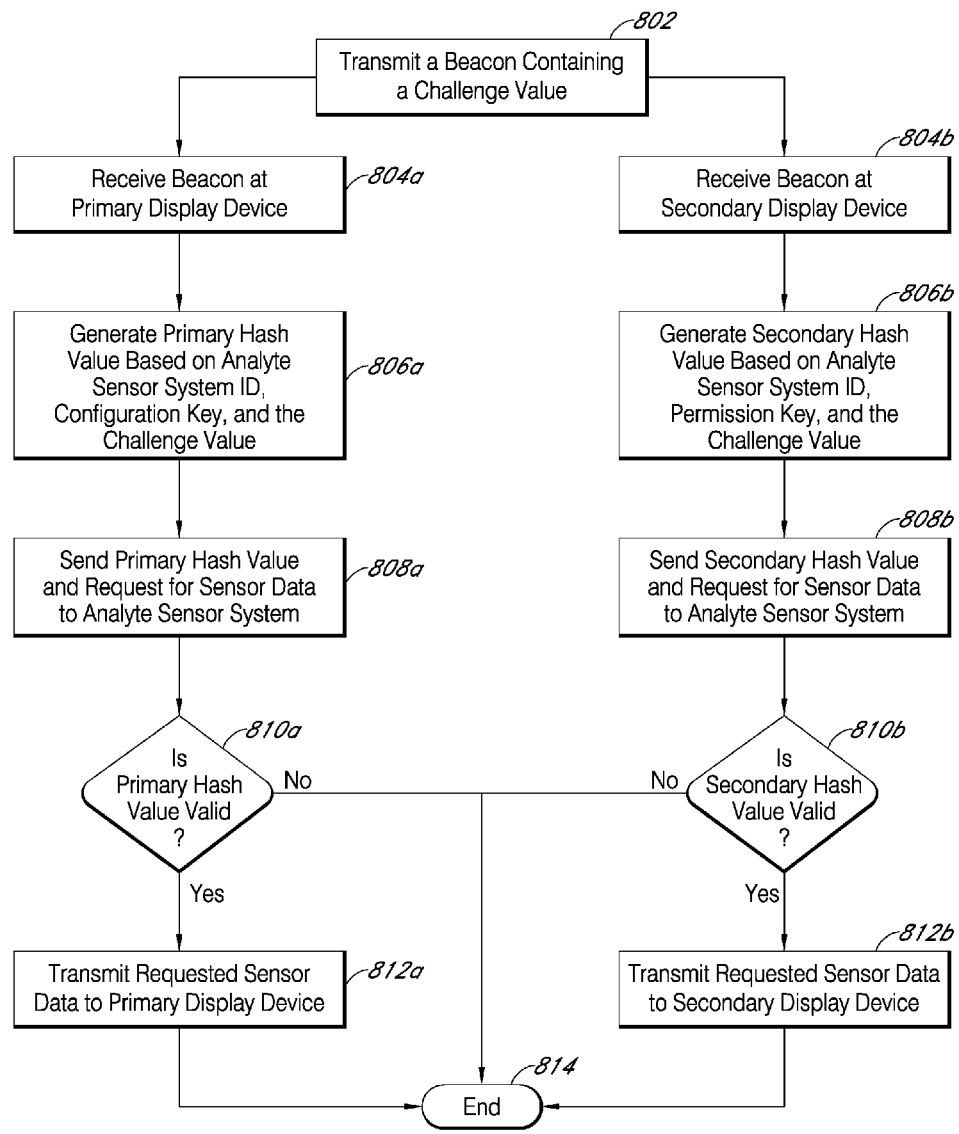
FIG. 8 is flowchart of an exemplary method for establishing an authenticated communication channel between an analyte sensor system and a primary or secondary display device.

FIG. 8 is flowchart of an exemplary method for establishing an authenticated communication channel between an analyte sensor system 8 and a primary device 16 or a secondary display device 14, 18. In block 802, the analyte sensor system 8 transmits a beacon containing a challenge value generated, for example as described above in FIG. 7. This beacon may be received at a primary display device 16 and/or secondary display device 14, 18 as shown in blocks 804*a* and 804*b*.

If received at a primary display device 16, the primary display device 16 may generate a primary hash value in block 806*a*. The primary hash value may be generated using a hash algorithm based on one or more of an identifier of the analyte sensor system 8, a key value, and the challenge value received in the beacon as shown in block 808*a*. The identifier may be associated with or derived from a unique identifier, such as an identifier of the analyte sensor system 8 imprinted on a housing of sensor electronics module 12 as described above.

The hash algorithm may further generate the primary hash value based on other information and identifiers such as an identifier associated with the primary display device to more easily allow an analyte sensor system 8 to determine a display type or the various or limited capabilities of the primary display 16.

The analyte sensor system 8 may have a list of allowable display identifiers or codes stored in memory. For example, a key value may be specific to a primary display device 16 type. For example, the key value may be a configuration key that is provided in the primary display device 16 by the manufacturer to permit the primary display device 16 to be used to control and configure the analyte sensor system 8. That is, the use of the configuration key may identify the display device 16 as a primary display device to the analyte sensor system 8, thereby determining the type of data exchanged and functionality allowed between the analyte sensor system 8 and the primary display device 16.

The secondary display device 14, 18 may also generate a secondary hash value in block 806*b*. The secondary hash value may be generated using a hash algorithm based on an analyte sensor system 8 identifier, a key value specific to the secondary display device 14, 18 type, and the challenge value. The key value may be a "permission" key that is different than the configuration key associated with a primary device and may be provided in the secondary display device 14, 18 by the manufacturer or a software supplier of software implemented on the secondary display device. The permission key may identify the display device 14, 16, 18, 20 as a secondary display device 14, 18 and indicate to the sensor system 8 that the secondary display device 14, 18 has permission to display glucose data to a user.

In one exemplary environment, there may be multiple different types of primary devices and multiple different types of secondary devices that can be permitted to communicate with the sensor system 8. Each of the secondary devices may have different permission keys to identify the type of the device and accompanying features/limitations that may be facilitated or enforced in part by the analyte sensor system 8 via instructions stored in the analyte sensor system and executed by a processor of the analyte sensor system. The hash algorithm may further generate the secondary hash value based on other information such as a display identifier that may provide additional information about the functionality of the display to further distinguish between display device 14, 16, 18, 20 types.

In block 808*a* and 808*b*, after the hash values have been generated, the primary and secondary display devices 14, 16, 18, 20 may send the hash values to the analyte sensor system 8. The analyte sensor system 8 may also generate its own hash values for each type of display that the analyte sensor system 8 is expecting to receive a request from (referred to herein from time to time as "expected hash values"). In this case, the analyte sensor system 8 may generate an expected hash value for a primary display device 16 and an expected hash value for a secondary display device 14, 18. The expected hash values may be compared to the hash value(s) received from the primary or secondary display device(s), as shown in blocks 810a and 810b.

If a received hash value matches none of the expected hash values, then the method ends in block 814 and no data is sent by the analyte sensor system 8 as the authentication failed. If the received hash value matches one of the expected hash values, then the communication request from the display device can be considered authenticated and a communication channel opened between the sensor system 8 and display device and data may be sent between the analyte sensor system 8 the primary display device 16 or secondary display device 14, 18 as shown in blocks 812a and 812b, respectively.

Further to block 812a and 812b, once authenticated, the type of data exchanged between the analyte sensor system 8 and the display device 14, 16, 18, 20 may depend on the type of display device (e.g., primary or secondary). For example, as stated above, in some embodiments the analyte sensor system 8 can be permitted to request calibration information (e.g., external calibration reference values) from a primary display device 16 but not from a secondary display device 14, 18. Indeed, if calibration data points are received from the display device 14, 16, 18, 20 identified as a secondary device, the analyte sensor system 8 may refuse or ignore the data. Furthermore, different types of data may be exchanged based on the display device 14, 16, 18, 20 type as each type of display device 14, 16, 18, 20 may have different limitations and be configured to display glucose measurement data in different ways. Suitable methods and systems for sending different types of data depending upon the type of display device that can be used herein are described in further detail in U.S. Patent Publication No. 2009/0240120, filed on Feb. 20, 2009, the entire content of which is hereby incorporated by reference.

As discussed above, a configuration key or permission key may be used to identify a display device as a type of display device (primary or secondary) or even if the display device is authorized to exchange data with the sensor system 8. That is, a configuration key or permission can be associated with a pre-approved device permitted to communicate with the sensor system. A list of approved keys can be stored in memory of the sensor system 8, and if a device attempting to authenticate with the sensor system does not have an approved key, then the device can be prevented from pairing with the sensor system.

In some implementations, multiple different devices can be approved for use with the sensor system 8. In such a case, the sensor system 8 can include multiple keys stored therein; for example, one key for each type of approved device.

The keys can be stored in a priority order in accordance with some implementations. During authentication, for example as described with respect to block 808 in FIG. 13, the sensor system 8 generates hash value using a key having the top priority in the key list (e.g., is on top of the list). If the hash value does not match the hash value received from the display device, then the sensor system generates another hash value using the next highest priority vendor code. The process repeats until either there is a match or all of the vendor codes are used without a match. In the latter case, there will be no authentication between the devices. In one example, the sensor system can include 20 different keys. Thus, it is possible that 20 different keys may be generated during an authentication.

To facilitate matching of keys, the key priority list can be adaptive. For example, the key that was used to generate a matching hash value can made the top priority key. That way, during the next authentication process, the key is the first key used to generate the sensor system has value in step 808 of FIG. 8, for example, and if there is a match, then no further hash values need be generated.

Limiting Communication with Multiple Primary and Secondary Display Devices

As described above, the analyte sensor system 8 may reserve just a fraction (represented by a data transmission window interval $T_{window}$) of the update interval $T_{update}$ for exchanging data with display devices 14, 16, 18, 20. Within this data transmission window interval $T_{window}$, an analyte sensor system 8 may be able to communicate with multiple display devices 14, 16, 18, 20. However communicating with multiple display devices 14, 16, 18, 20 may consume significant amounts of power. Some embodiments may limit the amount of display devices 14, 16, 18, 20 that may communicate with the analyte sensor system 8 during an interval $T_{window}$. In one embodiment, the length of the data transmission window interval $T_{window}$ may be limited by the analyte sensor system 8. In another embodiment, the analyte sensor system 8 may refuse requests from display devices 14, 16, 18, 20 once the analyte sensor system 8 has already communicated with a predetermined threshold number of display devices (e.g., three display devices during a transmission window $T_{window}$).

Figure 9:
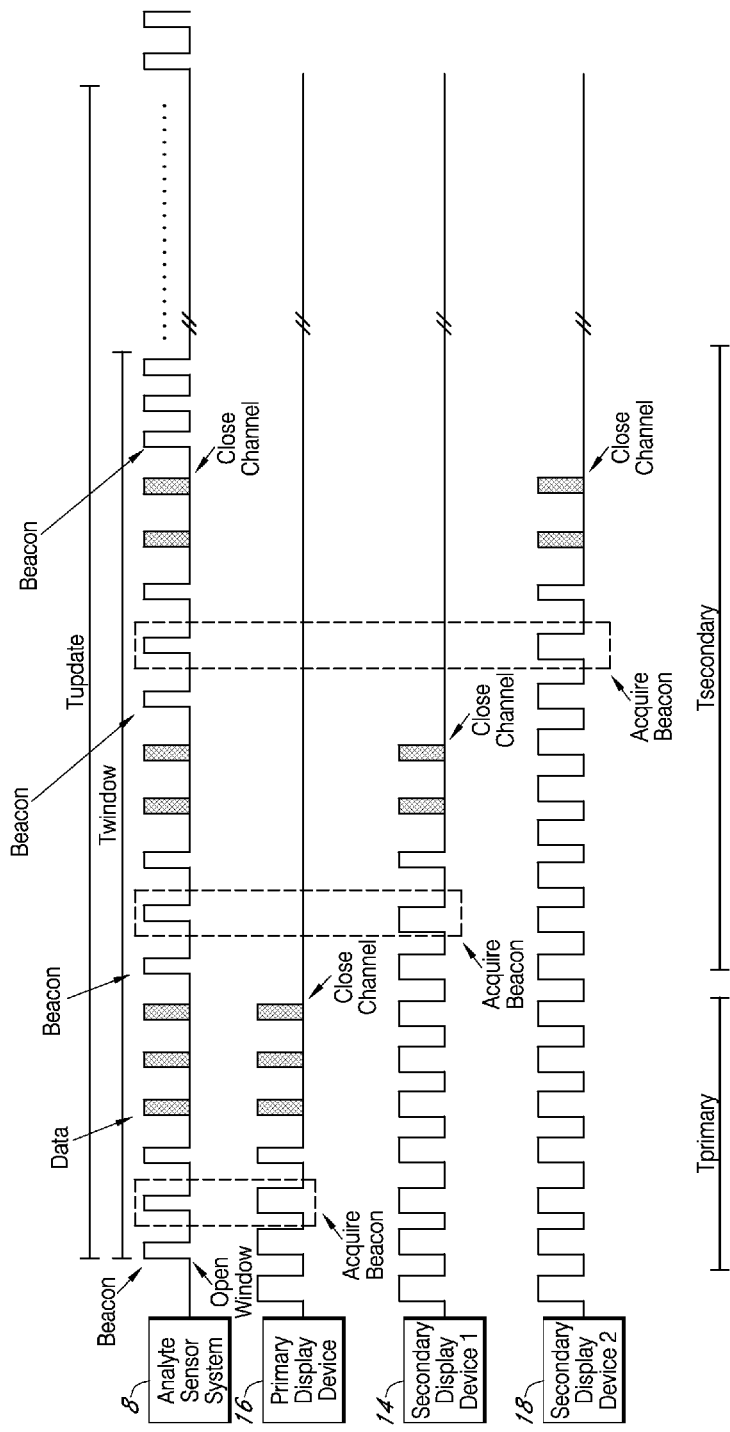
FIG. 9 is a timing diagram showing an exemplary scheme for exchanging data between an analyte sensor system and a plurality of display devices.

FIG. 9 is a timing diagram showing an exemplary scheme for exchanging data between an analyte sensor system 8 and a plurality of display devices 14, 16, 18. The analyte sensor system 8 may be configured to send and receive data during specified time slots. During an update interval $T_{update}$ (which may be at the beginning or end of the interval, for example), an analyte sensor system 8 may begin transmitting beacons as described above. A primary display device 16 may successfully receive the beacon (e.g., after the analyte sensor system 8 sends out two beacons as illustrated in FIG. 9) and send a data exchange request to the analyte sensor system 8 within the third time slot of the primary device's timing diagram. Once the request has been received and the primary display device 16 has been authorized, data may be exchanged between the two devices as indicated by the shaded time slots. As an illustrative example, the data in the first data time slot may include the most recent glucose measurement values and data in subsequent time slots may include calibration data or other control or configuration data. Once the analyte sensor system 8 and the primary display device 16 have finished exchanging requested data, the communication channel with the may be closed.

If there is still time remaining in the data transmission window interval $T_{window}$, the analyte sensor system 8 may resume sending beacons. As shown in FIG. 9, a first secondary display device 14 may be attempting to communicate with the analyte sensor system 8 and begin looking for the beacon at the beginning of $T_{window}$. In this case, while the first secondary display device 14 may receive the beacon at the same time as the primary display device 16, the analyte sensor system 8 may ignore subsequent requests from the first secondary display device 14 if it is already communicating with a primary display device 16. As will be further described below, in some embodiments, the type of display device may not be a factor in determining who first establishes the communication channel. Rather, in one embodiment, the display device that responds to the beacon first will be able to establish the communication channel and other devices may have to wait. As such, with reference to FIG. 9, if the first secondary display device 14 responds to the beacon before the primary display device 16, then a channel would be established initially with the first secondary display device 14. If the primary display device 16 responds first, the first secondary display device 14 may continue to listen for a beacon from the analyte sensor system 8 until it is authenticated by the analyte sensor system 8 and a channel is established between the analyte sensor system 8 and the first secondary display device 14. As shown in FIG. 9, the first secondary display device 14 may receive a beacon and establish a channel after the analyte sensor system 8 has finished communicating with the primary display device 16. The first secondary display device 14 may then exchange data with the analyte sensor system 8 for one or more time slots and subsequently close the channel.

If there is time remaining in the transmission window after finishing communicating with the first secondary display device 14, then the analyte sensor system 8 may resume sending beacons.

A second secondary display device 18 may additionally be attempting to communicate with the analyte sensor system 8 and begin searching to acquire a beacon during $T_{window}$. The second secondary display device 18 may continuously look for the beacon until the analyte sensor system 8 finally acknowledges and authenticates the second secondary display devices 18 after communicating with the primary display device 16 and the first secondary display device 14. Once authenticated, the second secondary display device 18 may exchange data with the analyte sensor system 8 and close the channel. This process may continue with other display devices 20 until a specified communication interval $T_{window}$ ends and the analyte sensor system 8 stops sending beacons until the beginning of another transmission window (e.g. at the beginning of the next update time interval $T_{update}$).

To conserve power, the number of display devices to which the analyte sensor system 8 communicates may be limited in several ways. For example, the analyte sensor system 8 may stop transmitting beacons or responding to data exchange requests after exchanging data with a predetermined number of display devices 14, 16, 18, 20. For example, the analyte sensor system 8 may only be allowed to communicate with a maximum of three devices during each data transmission window interval $T_{window}$.

The maximum number of display devices that can communicate during a transmission window interval can be variable. The variable can be set during manufacturing of sensor electronics module 12, can be user configurable by using display device 14, 16, 18, 20, for example, or can be automatically adjusted by sensor system 8 or display device 14, 16, 18, 20 based on one or more criteria. The criteria can include a monitored battery level of the analyte sensor system 8. For example, if the battery level is below a threshold, the analyte sensor system 8 may be configured to only communicate with one display device 14, 16, 18, 20. The criteria can include: (i) one or more errors detected by sensor system 8 or display device 14, 16, 18, 20, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), and (ix) type of display device.

In addition, limiting communication based on the battery level may be done by shortening the transmission window $T_{window}$, restricting the types of devices that may communicate with the sensor system, limit the types of data that can be exchanged between the sensor system and display devices 14, 16, 18, 20, or the like.

It should be appreciated that while the above functionality has been described with respect to dividing and restricting communication based on time slots, the principles described herein may apply to other communication protocols that use other multiplexing techniques such as frequency division multiplexing.

Furthermore, while FIG. 9 shows first communicating with a primary display device 16 and then two secondary display devices 14, 18, it should be appreciated that the order and type of display devices may not matter. As such, the analyte sensor system 8 may communicate first with a secondary display device 14 and then with a primary display device 16. In some embodiments, the analyte sensor system 8 may communicate only with a primary display device 16 during the communication interval $T_{primary}$. In other embodiments, the analyte sensor system 8 may communicate with only secondary display devices 14, 18 during the communication interval $T_{secondary}$.

In some cases it may be important to always allow a primary display device 16 to communicate during a transmission window. As such, the analyte sensor system 8 may implement a priority scheme to ensure the analyte sensor system 8 communicates with a primary display device 16 during the transmission window. In one embodiment, the analyte sensor system 8 may establish a specified time interval ($T_{primary}$) reserved for communication with a primary display device 16 within the transmission window interval $T_{window}$. In $T_{primary}$, which may be at the beginning of the transmission window $T_{window}$, the analyte sensor system 8 may be configured to only respond to and authenticate with a primary display device 16 and ignore other requests. After the $T_{primary}$ interval expires, secondary display devices 14, 18 may have the opportunity to establish a channel in addition to the primary display device.

It may be further necessary to restrict the use of a secondary display device 14, 18 when a primary display device 16 is capable of exchanging data with an analyte sensor system 8. For example, the primary display device 16 may incorporate functionality such as special alerts or alarms that help to ensure that a user maintains safe glucose levels. Regulations or safety guidelines may therefore require that the primary display device 16 always be used. As such, to help ensure the primary display device 16 is being used, the analyte sensor system 8 may only allow communication with a secondary display device 14, 18 if the analyte sensor system 8 has already sent glucose information to a primary display device 16 in a given transmission window $T_{window}$.

When sensor components are replaced (e.g. a new sensor 10 used in sensor system 8), a new sensor session may be established. In some embodiments, communication of glucose values to secondary devices 14, 18 may be disallowed until initiating of the sensor session is performed between a primary display device 16 and sensor system 8. The initiation process may include providing calibration data and setting alert thresholds for the sensor session. Once the session has been initiated using a primary display device 16, secondary display devices 14, 18 may be allowed to exchange data with the sensor system 8, such as receive glucose measurements and perform various functions (e.g., display estimated glucose values (EGVs), trend graphs, arrows, sound alarms) even if the primary display device 16 is not currently in proximity to or exchanging data with the analyte sensor system 8. However, certain functionality of the secondary display device 14, 18 may be restricted. As such, communication between the secondary display device 14, 18 and the analyte sensor system 8 may be based on communication between the primary display device 16 and the analyte sensor system 8. In another embodiment, the analyte sensor system 8 may not actively measure glucose concentration values until the sensor session is initiated with a primary display device 16. In this case, the analyte sensor system 8 may not transmit any information and a secondary display 14, 18 would not be able receive any information or establish a channel. In this case, a secondary display device 14, 18 would not be able to communicate until the sensor session was initiated by a primary display device 16.

Figure 10:
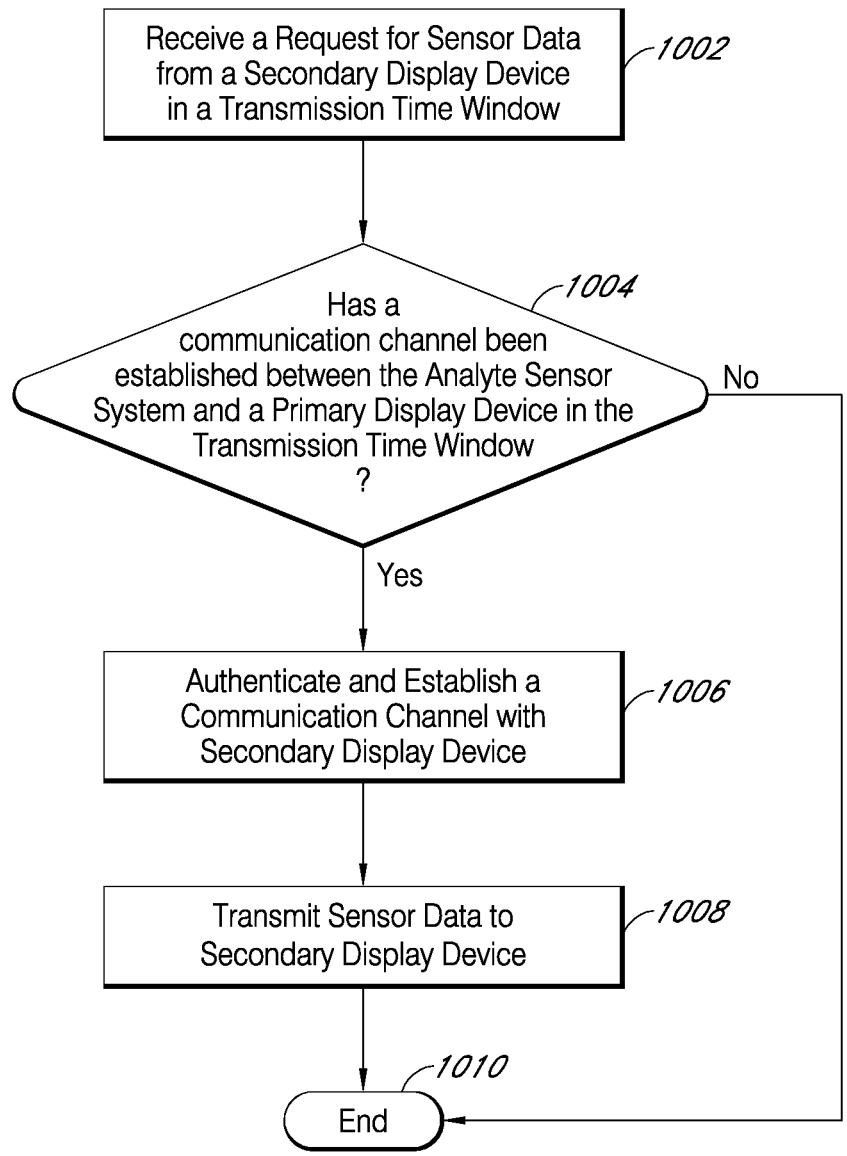
FIG. 10 is a flowchart of an exemplary method for communication between an analyte sensor system and a secondary display device.

FIG. 10 is a flowchart of an exemplary method for communication between an analyte sensor system 8 and a secondary display device 14, 18. In block 1002, an analyte sensor system 8 may receive a request for sensor data from a secondary display device 14, 18 during a transmission window. In block 1004, the analyte sensor system 8 may determine whether a communication channel been established between the analyte sensor system 8 and a primary display device 16 during the transmission window. If no communication channel was established with a primary display device 16, then the method may end in block 1010 and the analyte sensor system 8 may refuse to communicate with the secondary display device 14, 18. For example, if a period of time of the transmission window is reserved for communication with a primary display device 16 and no communication takes place, any subsequent requests by secondary display devices 14, 18 may be refused. If a communication channel has been established with a primary display device 16 during the transmission window, then the analyte sensor system 8 may authenticate and establish a communication channel with the secondary display device 14, 18 as shown in block 1006. In block 1008, the analyte sensor system 8 may then transmit sensor data to the secondary display device 14, 18.

Active Primary Display Device Determination

In some embodiments, while many display devices may be permitted to communicate with sensor electronics module 12, it may be desirable to limit use of primary display devices with a sensor electronics module to one at any given time. Some embodiments provide rules to determine if a given primary display device is currently the active primary display device. If a user tries to perform any action from a non-active controller, the user may be informed that the device is not currently the active primary display device and presented instructions via the device to make the device the active controller. Switching active primary devices may be desirable if the user loses the active primary device or wants to switch to a newer primary display device, for example.

The following is one implementation of an active controller determination process. Here, the sensor system 8 maintains an identifier ("primary display device id") specific to the currently active primary display its memory. During an established communication channel with the sensor system 8, the primary display device may request from the sensor system the currently active primary display id. In one implementation, the primary device requests an alerts data page that includes information indicative of current alert settings as well as the active primary display id stored in the sensor system. If the primary display device id in the message indicates that the sensor system 8 has been already communicating with a primary display (indicated by a non-matching primary display device id) or if no other primary display device has been in communication (indicated by all zeros for the id, for example), the primary display will display instructions to the user to confirm if the user intends to make this display device the new active primary display device. If the user confirms, the primary display device generates a new two byte random id and sends that to the sensor system 8 as the primary display device id and the sensor system switches to the new primary display device id.

After switching to a new primary display device id, the sensor system 8 sends a message indicative of the change for a predetermined number of subsequent window beaconing cycles, such as three beacon cycles. The message may be a predetermined bit within the data page of each beacon indicating the change. A primary display device that receives the message may request the primary display device id stored in the sensor system from the sensor system and compare the received primary display device id to the primary device id stored in its own memory. If the primary display id from the sensor system does not match its own primary display id, then the primary display can display instructions to the user indicating this change and make itself into a non-active primary display. In an implementation, a non-active primary display will then only have the functionality of a secondary display device. If the user needs to start using this display as an active primary display again, the user may perform a fresh pairing with the sensor system 8 as discussed above.

In some implementations, if a primary display misses more than a predetermined number of beacon cycles, such as three beacons cycles, the primary display device will then automatically confirm that it is still the active primary display device using the above-described process.

Display Device Handoff

As the data transmission window interval $T_{window}$ of an analyte sensor system 8 may only be a small fraction (e.g., 30 seconds) of a much longer update interval (e.g., five minutes), it may be desirable for a display device 14, 16, 18, 20 to have specific information about the time when $T_{window}$ opens to know when to listen for the beacon sent by the analyte sensor system 8.

As described above, when the sensor electronics module is first activated (e.g., when it is powered for the first time or after a battery replacement), there may be a process completed using a primary display device 16 to establish communications and synchronize the timing of later transmission windows. For example, upon activation, the transceiver 316 may initially continuously emit beacons or enter the transmission window more frequently until communication is established with a primary display device 16. In this way the primary display device 16 may not need specific information about when the transmission window $T_{window}$ opens. Once the channel is initially opened, the analyte sensor system 8 may send synchronization information to the primary display device 16, or synchronization information may be derived based on the timing of beacon transmissions, so that the primary display device knows when the transmission window $T_{window}$ will be open. The primary display device 16, may therefore be able to know the timing for establishing communication with the analyte sensor system 8 over the life of the battery (and over several sensor sessions).

The synchronization information may not be initially available to a secondary display device 14, 18; for example, if the secondary device 14, 18 has not yet established communication with the sensor system. In such a case, the secondary display device 14, 18 may not know when a transmission window starts and consequently search for beacons at the wrong time. This can cause the secondary display device 14, 18 to miss the opportunity to establish a communication channel with the sensor system 8 during the transmission window. As such, some embodiments allow the secondary device to learn transmission window synchronization information. The primary display device 16 may provide the synchronization information to the secondary display device 14, 18.

In one embodiment, the display of the primary display device 16 may display an indication of the time remaining until the next transmission window of the analyte sensor system 8 opens based on the synchronization information previously gathered from the sensor system and now stored in the primary display device. The indication can be a graphical indication of a timer (graphical bar, pie chart, etc.) timing down to when the window is scheduled to open next, or can be a numerical timer incrementing the time left until the window is scheduled to open next. A user of a secondary display device 14, 18 may monitor the time remaining and then provide an input to the secondary display device 14, 18 (e.g., press a button or other activation trigger) when the transmission window of the analyte sensor system 8 is about to open. The user input may activate the secondary display device 14, 18 to begin searching for a beacon.

Figure 11:
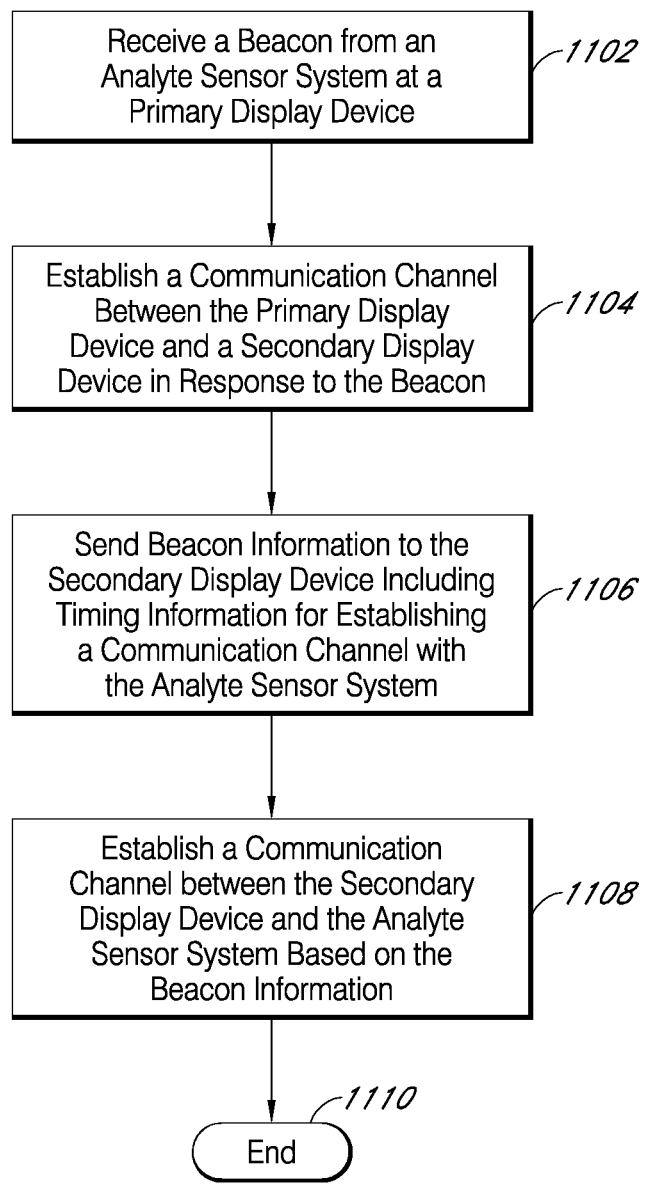
FIG. 11 is a flow chart of an exemplary method for providing sensor transmission time window information from primary display device to a secondary display device.

In another embodiment, the primary display device 16 may electronically pass off sensor system synchronization information to the secondary display device 14, 18 via wired or wireless communication. FIG. 11 is a flow chart of an exemplary method for providing sensor system synchronization information from primary display device 16 to a secondary display device 14, 18. In block 1102, the primary display device 16 may receive a beacon from an analyte sensor system 8. Synchronization information about the timing of the transmission window of the analyte sensor system 8 (e.g., the time of the beginning of each data transmission window interval $T_{window}$) may be included in or derived from the beacon. In block 1104, a communication channel may be established between the primary display device 16 and a secondary display device 14, 18 that wants to obtain the timing information for establishing a communication channel with the analyte sensor system 8. In block 1106, the primary display device 16 may then send beacon information to the secondary display device 14, 18 that may include timing information for establishing a communication channel with the analyte sensor system 8. The beacon information may include the current transmission time (e.g., from the point at which the primary display opened its channel) and an update interval equal to the amount of time remaining until the glucose device's next transmission. In addition, further information may be exchanged between the secondary display device 14, 18 and the primary display device 16 such as past glucose data information that may be stored on the primary display device 16.

Once the secondary display device 14, 18 has received the beacon information, the secondary display device 14, 18 may then establish a communication channel with the analyte sensor system 8 based on the beacon information as shown in block 1108. Moreover, in some embodiments, an authentication procedure, similar to the authentication procedure described above, may be used between the primary display device 16 and the secondary display device 14, 18 to establish communication in block 1104.

While the above description primarily describes a handoff from a primary device to a secondary display device, it is understood that this description is illustrative only, and that the handoff can likewise be between a first primary display device and a second primary display device, should a new primary display device be desired to be used. Similarly, the handoff can be performed between to secondary display devices in some implementations.

Interleaving Transmission and Measurement Sessions

The more operations that are performed substantially simultaneously on the analyte sensor system 8, the more power may be consumed during that time. For example, significant power consumption may occur if the analyte sensor system 8 is transmitting sensor data during the same time that the analyte sensor system 8 is sampling and/or processing sensor readings. To reduce strain on battery usage or the need to use a battery that can provide large amounts of power at a given time, some embodiments interleave transmission and measurement sessions to avoid simultaneously transmitting while taking measurement and processing the measurements. This may dictate that the analyte sensor system 8 transmits only between sessions where sampling of sensor data and any subsequent processing is performed. In addition, the amount of time of the transmission window may be limited to ensure that it does not overlap with sampling and processing.

Figure 12A:
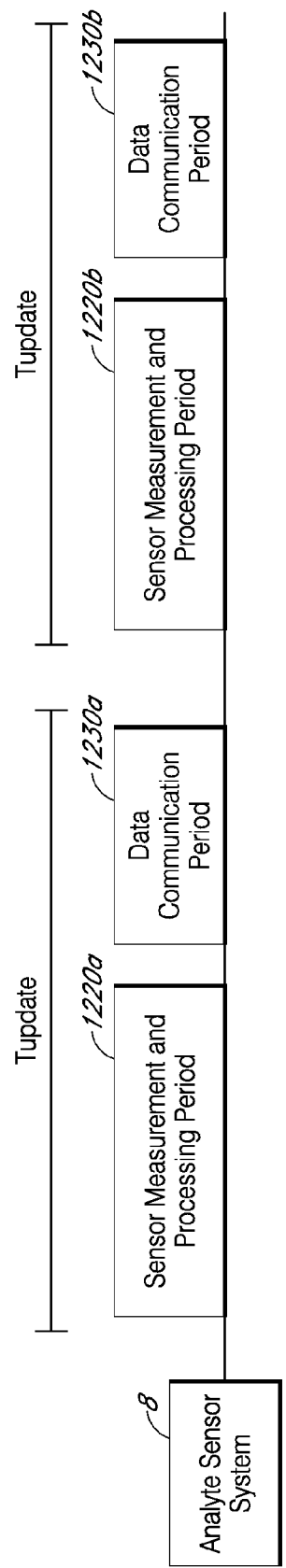
FIG. 12A is a timing diagram of an exemplary timing scheme for transmitting data and obtaining and processing analyte sensor measurements.

FIG. 12A is a timing diagram of an exemplary timing scheme for transmitting data and obtaining and processing analyte sensor measurements. As shown in FIG. 12A, each update interval $T_{update}$ may be divided into two periods: a sensor measurement and processing period 1220a, 1220b and a data communication period 1230a, 1230b. If the $T_{update}$ interval is five minutes, then a four minute and 30 second measurement cycle 1220a may be followed by a thirty second transmission window 1230a, for example. Measurement circuitry 310 may be powered down during the transmission window 1230a and the transceiver 316 may be powered down during a measurement cycle 1220a. This may be repeated for each update interval.

In some cases the length of time of the measurement cycles 1220 may vary. In these cases the length of time of the transmission window 1230 may be adjusted to ensure it does not overlap with the measurement cycle. Further, the analyte sensor system 8 may send information in the beacons about the total length of time the current transmission window will be open or how much time remains until the current transmission window closes.

Figure 12B:
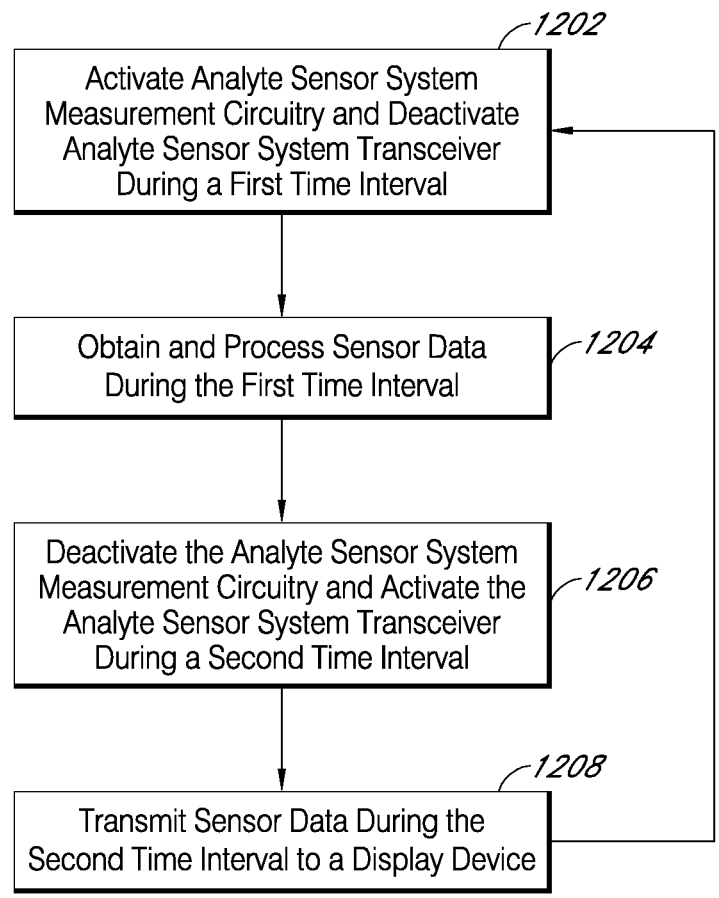
FIG. 12B is a flowchart of an exemplary method for interleaving an analyte sensor measurement and processing period with a data communication period for transmitting glucose measurement values.

FIG. 12B is a flowchart of an exemplary method for interleaving an analyte sensor measurement and processing period with a data communication period for transmitting glucose measurement values. In block 1202, the analyte sensor system 8 may activate sensor measurement circuitry 310 and deactivate the transceiver 316 during a first time interval. In block 1204, the analyte sensor system 8 may obtain and process sensor readings during the first time interval. Once the sampling and processing is completed, the analyte sensor system 8 may deactivate the sensor measurement circuitry 310 and activate the transceiver 316 during a second time interval corresponding to a data transmission window. In block 1208, the analyte sensor system 8 may then transmit sensor data during the second time interval to a display device 14, 16, 18, 20. This process may be continuously repeated for each update interval.

It should be appreciated that a full time interval may not be needed for sensor measurement and processing. As such, the measurement circuitry 310 may further be deactivated for the portion of the time interval that it is not being used. Accordingly, the activating and deactivating in FIG. 12 B may include selectively powering down/up some or all of the sensor measurement circuitry 310 and transceiver 316, or selectively placing the sensor measurement circuitry 310 and transceiver 316 into a low power mode such as a sleep mode.

Providing Missing Data to a Display Device

An analyte sensor system 8 may continuously store past glucose measurements. A display device 14, 16, 18, 20 may not always have the full history of glucose data stored on the analyte sensor system 8. For example, the display device 14, 16, 18, 20 may have been out of range of the analyte sensor system 8 for a time period or is being newly used in the middle of a sensor session and wants to access the missing data stored on the analyte sensor system 8.

FIG. 13A shows an example of data structures 1310a, 1310b, and 1310c that may be stored on an analyte sensor system 8 that include glucose measurement values. The data structures 1310a, 1310b, and 1310c may be formatted as data files, each with a series of glucose measurement values. The data structures 1310a, 1310b, and 1310c may hold glucose measurement values that correspond to a specific time period over which the stored glucose measurement values were obtained. For example, each data structure 1310a, 1310b, and 1310c may correspond to a twenty-four hour period of glucose measurements.

One embodiment of the invention provides for allowing the display device 14, 16, 18, 20 to request and receive past glucose measurements from the analyte sensor system 8 in addition to the normal transmission of the most recent glucose measurement value.

FIG. 13B is a flowchart of an exemplary method of transmitting sensor data from an analyte sensor system 8 to a display device 14, 16, 18, 20. The display device 14, 16, 18, 20 may be able to determine a range of missing glucose measurement-related data that it desires from the analyte sensor system 8. In block 1302, an analyte sensor system 8 may receive a request for previous glucose measurement values 1312 in addition to glucose measurement value normally included in the periodic data transmission. In block 1304, the analyte sensor system 8 may then transmit a data set corresponding to some time interval over which measurement values are stored that includes the requested glucose measurement values. The analyte sensor system 8 may be formatted specially for transmission (e.g., a compressed). In one aspect, an entire data set 1310a (e.g., a data file) may be transmitted as opposed to just the requested range of glucose measurement related data. As such, the transmitted data set 1310 may include a range of glucose measurement related data that exceeds the requested range. This may reduce processing time and power needed to retrieve and send only the specifically requested range of glucose measurement related data. This may provide for significant power savings which may allow the battery of sensor system 8 to last longer.

Furthermore, as described above, a primary display device 16 may also be configured to provide missing data values to a secondary display device 14, 18 to avoid wasting processing power on the analyte sensor system 8 to transmit the missing data points.

Technical Support Data Exchange

In some implementations, the sensor system may monitor and record possible technical issues associated with the sensor system 8. The technical issues may be recorder in a technical support log file stored in memory of the sensor system A user of the sensor system 8 may recognize a problem or otherwise determine a need to contact technical support to resolve the problem or need. At that time, the technical support may want the user to obtain some or all of the technical support log file from the sensor system 8. However, since the sensor system 8 may not have a display and a display device may only be able to communicate with the sensor system infrequently (only when the next transmission window opens), the user may have to wait a significant amount of time before being able to obtain the technical support log file from the sensor system and display information in the file on the display device or transmit (for example over the Internet) some or all of the technical file log from the display device to a computer associated with the technical support.

In addition, it may be desirable to collect sensor data and/or the technical support log file to support analysis of sensors or debugging of the sensor system software or firmware. In these situations, it may be desirable to be able to collect this information without annoying the user (for example, by not requiring the user to press buttons for downloads).

In some implementations, the sensor system 8 can send a message to a display device anytime the sensor system determines that technical support information stored in the technical support log file is worth having on the display device. For illustrative purposes, such an occurrence can include: (i) the sensor system going out of calibration after a calibration; (ii) the sensor system not going out of calibration, but the difference between a reference value and a corresponding estimated glucose value exceeds a predetermined amount; (iii) the sensor system software or firmware encounters a particular type of error, even if the system determines that it has resolved the error; (iv) the sensor system firmware or software encounters an error that results in alerting the user to the error via the display device; and (v) periods of time during use of a sensor where the sensor system detects noise or other kinds of aberrations above a predetermined level.

When the display device receives the message, it can be programmed to automatically request some or all of the support file log. The display device may also automatically send the support log file to the technical support computer over a communication network (e.g., cellular network is the display device is a smart phone or over the Internet if the display device is a PC connected to the Internet). If a communication network is not immediately available, the display device can send the support log file technical support upon connecting to the display device to suitable communication network. This way, the display device and/or technical support may already have the technical information on hand when a user calls technical support to resolve a problem or need.

In some embodiments, the message sent by the sensor system is a bit in a data page sent from the sensor system indicative of the presence of the technical support information. The data page is the beacon data page in some implementations. Having the bit can provide the flexibility to obtain the technical support data without having to specify all the conditions under which the display device needs to obtain the technical support log file. For example, the display device can also choose not to obtain the technical support log file from the sensor system if similar conditions occurred in the recent past and technical support was already performed the previous time.

Methods and devices that may be suitable for use in conjunction with aspects of the preferred embodiments are disclosed in U.S. Pat. No. 4,994,167; U.S. Pat. No. 4,757,022; U.S. Pat. No. 6,001,067; U.S. Pat. No. 6,741,877; U.S. Pat. No. 6,702,857; U.S. Pat. No. 6,558,321; U.S. Pat. No. 6,931,327; U.S. Pat. No. 6,862,465; U.S. Pat. No. 7,074,307; U.S. Pat. No. 7,081,195; U.S. Pat. No. 7,108,778; U.S. Pat. No. 7,110,803; U.S. Pat. No. 7,192,450; U.S. Pat. No. 7,226,978; and U.S. Pat. No. 7,310,544.

Methods and devices that may be suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0142142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032717-A1; U.S. Patent Publication No. US-2007-0032718-A1; U.S. Patent Publication No. US-2007-0059196-A1; U.S. Patent Publication No. US-2007-0066873-A1; U.S. Patent Publication No. US-2007-0093704-A1; U.S. Patent Publication No. US-2007-0197890-A1; U.S. Patent Publication No. US-2007-0173710-A1; U.S. Patent Publication No. US-2007-0163880-A1; U.S. Patent Publication No. US-2007-0203966-A1; U.S. Patent Publication No. US-2007-0213611-A1; U.S. Patent Publication No. US-2007-0232879-A1; U.S. Patent Publication No. US-2007-0235331-A1; U.S. Patent Publication No. US-2008-0021666-A1; and U.S. Patent Publication No. US-2008-0033254-A1.

Methods and devices that are suitable for use in conjunction with aspects of the preferred embodiments are disclosed in U.S. patent application Ser. No. 09/447,227 filed Nov. 22, 1999 and entitled "DEVICE AND METHOD FOR DETERMINING ANALYTE LEVELS"; U.S. patent application Ser. No. 11/654,135 filed Jan. 17, 2007 and entitled "POROUS MEMBRANES FOR USE WITH IMPLANTABLE DEVICES"; U.S. patent application Ser. No. 11/654,140 filed Jan. 17, 2007 and entitled "MEMBRANES FOR AN ANALYTE SENSOR"; U.S. patent application Ser. No. 11/543,396 filed Oct. 4, 2006 and entitled "ANALYTE SENSOR"; U.S. patent application Ser. No. 11/543,490 filed Oct. 4, 2006 and entitled "ANALYTE SENSOR"; U.S. patent application Ser. No. 11/543,404 filed Oct. 4, 2006 and entitled "ANALYTE SENSOR"; U.S. patent application Ser. No. 11/691,426 filed Mar. 26, 2007 and entitled "ANALYTE SENSOR"; U.S. patent application Ser. No. 11/691,432 filed Mar. 26, 2007 and entitled "ANALYTE SENSOR"; U.S. patent application Ser. No. 11/691,424 filed Mar. 26, 2007 and entitled "ANALYTE SENSOR"; and U.S. patent application Ser. No. 11/691,466 filed Mar. 26, 2007 and entitled "ANALYTE SENSOR".

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for authorizing analyte sensor data exchange between a first communication device associated with an analyte sensor and a second communication device configured to provide user access to analyte values and/or information derived from analyte values, comprising: sending a challenge value from a first communication device associated with an analyte sensor to a second communication device; generating a first hash value in the second communication device using, at least in part, one or more of the challenge value, an identifier of the first communication device, or a key value; sending the first hash value from the second communication device to the first communication device; generating, using the first communication device, a second hash value and a third hash value; comparing, using the first communication device, the second hash value and the third hash value to the first hash value; and sending analyte sensor data only if at least one of the second hash value or the third hash values matches the first hash value.

2. The method of claim 1, further comprising determining a type of the second communication device based on a match between the first hash value and the second hash value or a match between the first hash value and the third hash value.

3. The method of claim 1, wherein the key value is a first value if the second communication device is of a first type, and wherein the key value is a second value if the second communication device is of a second type.

4. The method of claim 1, wherein the first hash value is generated using a display identifier.

5. The method of claim 1, wherein the first communication device comprises a sensor electronics module, and wherein the sensor electronics module is configured to electronically couple to an analyte sensor and to generate an analyte data stream using the analyte sensor.

6. The method of claim 2, wherein sending analyte sensor data comprises sending analyte sensor data based at least in part on the type of the second communication device.

7. The method of claim 3, wherein the type of second device corresponds to one of a primary device or a secondary device, wherein the primary device is configured to communicate analyte calibration data to the first communication device, and wherein the first communication device is configured to reject analyte calibration data received from a secondary communication device.

8. A method for transmitting data between a first communication device associated with an analyte sensor and one or more second communication devices configured to provide user access to analyte values and/or information derived from analyte values, comprising: receiving a request from a second communication device of the one or more second communication devices to establish a communication channel for receiving analyte sensor data from the first communication device during a transmission window; and establishing the communication channel between the first communication device and the second communication device if a number of communication devices that previously received analyte sensor data from the first communication device during the transmission window is below a threshold.

9. The method of claim 8, wherein the second communication device comprises a secondary communication device.

10. The method of claim 8, further comprising: determining whether the second communication device is a primary communication device; and establishing, if the second communication device is a primary communication device, a communication channel with the second communication device even if a number of communication devices that previously received analyte sensor data during the transmission window is equal to or greater than the threshold.

11. The method of claim 8, wherein the first communication device comprises a sensor electronics module, the sensor electronics module configured to electronically couple to an analyte sensor and to generate an analyte data stream using the analyte sensor.

12. The method of claim 8, further comprising monitoring the number of communication devices that previously received analyte sensor data during the transmission window and comparing the number to the threshold.

* * * * *

UNITED STATES PATENT AND TRADEMARK OFFICE
CERTIFICATE OF CORRECTION

PATENT NO. : 9,974,018 B2
APPLICATION NO. : 13/624727
DATED : May 15, 2018
INVENTOR(S) : Kenneth San Vicente et al.

It is certified that error appears in the above-identified patent and that said Letters Patent is hereby corrected as shown below:

On page 3, Column 1 (Item (56)), at Line 15 (Approx.), Under Other Publications, change "ncorporated:" to --Incorporated:--.

In Column 8 at Line 8, Change "en" to --an--.

In Column 9 at Line 13, Change "acarboxyprothrombin;" to --a carboxyprothrombin;--.

In Column 9 at Line 17, Change "andrenostenedione;" to --androstenedione;--.

In Column 9 at Line 33, Change "diptheria/" to --diphtheria/--.

In Column 9 at Line 40, Change "perioxidase;" to --peroxidase;--.

In Column 9 at Line 49, Change "sissomicin;" to --sisomicin;--.

In Column 9 at Line 53, Change "duodenalisa," to --duodenalis,--.

In Column 9 at Line 61, Change "Trepenoma pallidium," to --Treponema pallidum,--.

In Column 9 at Line 62, Change "stomatis" to --stomatitis--.

In Column 10 at Lines 15-16, Change "(barbituates," to --(barbiturates,--.

In Column 10 at Line 31, Change "(FHIAA)." to --(5-HIAA).--.

In Column 32 at Line 20, Change "T-$_{window}$." to --T$_{window}$.--.

In Column 33 at Line 53, Change "substrates" to --substates--.

In Column 33 at Line 55, Change "substrates" to --substates--.

Signed and Sealed this
Twenty-first Day of August, 2018

Andrei Iancu
*Director of the United States Patent and Trademark Office*

CERTIFICATE OF CORRECTION (continued)
U.S. Pat. No. 9,974,018 B2

In Column 33 at Line 67, Change "substrates" to --substates--.

In Column 34 at Line 28, After "background" insert --.--.

In Column 34 at Line 55, After "cycles" insert --;--.

In Column 34 at Line 64, After "5 s" insert --.--.

In Column 36 at Line 6, Change "'A65834F '," to --'A65S34F',--.

In Column 48 at Line 6, After "system" insert --.--.